US007459145B2

(12) United States Patent
Bao et al.

(10) Patent No.: US 7,459,145 B2
(45) Date of Patent: Dec. 2, 2008

(54) MULTIFUNCTIONAL MAGNETIC NANOPARTICLE PROBES FOR INTRACELLULAR MOLECULAR IMAGING AND MONITORING

(75) Inventors: Gang Bao, Mableton, GA (US); Shuming Nie, Atlanta, GA (US); Nitin Nitin, Atlanta, GA (US); Leslie LaConte, Decatur, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 252 days.

(21) Appl. No.: 10/694,243

(22) Filed: Oct. 27, 2003

(65) Prior Publication Data
US 2005/0130167 A1 Jun. 16, 2005

Related U.S. Application Data

(60) Provisional application No. 60/421,361, filed on Oct. 25, 2002.

(51) Int. Cl.
*A61B 5/055* (2006.01)
(52) U.S. Cl. .................. 424/9.32; 424/1.11; 424/1.29; 424/1.37; 424/1.33; 424/1.65; 424/1.73
(58) Field of Classification Search ................ 424/1.11, 424/1.29, 1.45, 1.49, 1.53, 9.3, 1.65, 1.69, 424/9.1, 9.323, 9.32, 9.321, 9.322, 9.34, 424/9.36, 9.35, 9.362; 428/402, 402.2; 75/255
See application file for complete search history.

(56) References Cited

U.S. PATENT DOCUMENTS 6,576,221 B1 * 6/2003 Kresse et al. ............ 424/9.322

OTHER PUBLICATIONS

Davis et al (Chemistry of Materials, 1998, vol. 10, No. 9, pp. 2516-2524).*
Wunderbaldinger et al (Bioconjugate Chemistry, 2002, vol. 13, No. 2, pp. 264-268).*
Tyagi et al., 1996, "Molecular Beacons: Probes that Fluoresce upon Hybridization," Nat. Biotechnol. 14:303-308.
Tyagi et al., 1998, "Multicolor Molecular Beacons for Allele Discrimination," Nat. Biotechnol. 16:49-53.
Wadia et al., 2002, "Protein Transduction Technology," Opinion in Biotechnology 13:52-56.
Weissleder et al., 1991, "Target-Specific Superparamagnetic MR Contrast Agents," J Magn. Reson 22, 209-212.
Weissleider et al., 2001, "Molecular Imaging," Radiology 219:316-333.
Whaley et al., 2000, "Selection of Peptides with Semiconductor Binding Specificity for Directed Nanocrystal Assembly," Nature, 405:665-668.
Yee et al., 1999, "Self-Assembled Monolayers of Alkanesulfonic and -Phosphonic Acids on Amorphous Iron Oxide Nanoparticles," Langmuir 15: 7111-7115.

Zhao et al., 2002, "Differential Conjugation of Tat Peptide to Superparamagnetic Nanoparticles and Its Effect on Cellular Uptake," bioconjugate Chem. 13:840-844.
Alivisatos et al., 1996, "Organization of 'Nanocrystal Molecules' Using DNA," Nature 382, 609-611.
Alivisatos et al., 1996, "Semiconductor Clusters, Nanocrystals, and Quantum Dots," Science 271:933-937.
Becker-Hapak, et al., 2001, "TAT-Mediated Protein Transduction into Mammalian Cells," Methods. 24, 247-256.
Bonnet et al., 1998, "Kinetics of Conformational Fluctuations in DNA Hairpin-Loops," Proc. INatl. Acad. Sci., 95:8602-8606.
Bruchez, Jr. et al., 1998, "Semiconductor Nanocrystals as Fluorescent Biological Labels," Science 281, 2013-2015.
Bulte, et al. 1992, "Specific MR Imaging of Human Lymphocytes by Monoclonal Antibody-Guided Dextra-Magnetite Particles," Magn. Reson. Med. 25, 148-157.
Bulte, et al., 1997, "Magnetic Nanoparticles as Contrast Agents for MR Imaging," In Specific and clinical applications of magnetic carriers. (Editors: Häfeli, U. et al.) Plenum Press, New York, pp. 527-543.
Bulte, et al., 2001, "Magnetodendrimers Allow Endosomal Magnetic Labeling and in vivo Tracking of Stem Cells," Nat. Biotechnol. 19, 1141-1147.
Butterworth et al., 2001, "Preparation of Ultrafine Silica- and PEG-coated Magnetite Particles," Colloids and Surfaces A-Physicochemical and Engineering Aspects, 179:93-102.
Chan, et al., 1998, "Quantum Dot Bioconjugates for Ultrasensitive Nonisotopic Detection," Science 281, 2016-2018.
Chen et al., 2000, "Molecular Beacons: A Real-Time Polymerase Chain Reaction Assay for Detecting Salmonella," Analytical Biochem 280:166-172.
Coroiu, 1999, "Relaxivities of Different Superparamagnetic Particles for Application in NMR Tomography," J Magn Magn Mater 201, 449-452.
De Baar et al., 2001, "One-Tube Real-Time Isothermal Amplification Assay to Identify and Distinguish Human Immunodeficiency Virus Type 1 Subtypes A, B, and C and Circulating Recombinant Forms AE and AG," J. of Clin. Microbiology, 39(5):1895-1902.

(Continued)

*Primary Examiner*—D. L Jones
(74) *Attorney, Agent, or Firm*—Sutherland Asbill & Brennan LLP

(57) ABSTRACT

The present invention provides multifunctional magnetic nanoparticle probe compositions for molecular imaging and monitoring, comprising a nucleic acid or polypeptide probe, a delivery ligand, and a magnetic nanoparticle having a biocompatible coating thereon. The probe compositions may further comprise a fluorescent or luminescent resonance energy transfer moiety. Also provided are compositions comprising two or more such multifunctional magnetic nanoparticle probes for molecular imaging or monitoring. In particular, the nucleic acid or polypeptide probes bind to a target and generate an interaction observable with magnetic resonance imaging (MRI) or optical imaging. The invention thereby provides detectable signals for rapid, specific, and sensitive detection of nucleic acids, polypeptides, and interactions thereof in vivo.

54 Claims, 13 Drawing Sheets

OTHER PUBLICATIONS

Dressman et al., 2003, "Transforming Single DNA Molecules into Fluorescent Magnetic Particles for Detection and enumeration of Genetic Variations," PNAS, 100(15): 8817-8822.

Dubertret et al., 2001, "Single-Mismatch Detection Using Gold-Quenched Fluorescent Oligonucleotides," Nature Biotechnol. 19, 365-570.

Dyal et al., 2003, Activity of Candida rugosa Lipase Immobilized on gamma-Fe2O3 Magnetic Nanoparticles, J And Chem 125: 1684-1685.

Elghanian et al., 1997, "Selective Colorimeric Detection of Polynucleotides Based on the Distance-Dependent Optical Properties of Gold Nanoparticles," Science 277, 1078-1081.

Fang et al., 2000, "Using Molecular Beacons to Probe Molecular Interactions Between Lactate Dehydrogenase and Single-Stranded DNA," Anal. Chem., 72:3280-3285.

Goddard et al., 2000, "Sequence Dependent Rigidity of Single Stranded DNA," Phys Rev. Lett 85:2400-2403.

Han et al., 2001, "Quantum-dot-Tagged Microbeads for Multiplexed Optical Coding of Biomolecules," Nature Biotechnol. 19, 631-635.

Harris et al., 2001, "Traumatic Brain Injury-Induced Changes in Gene Expression and Functional Activity of Mitochondrial Cytochrome C Oxidase," J Neurotrauma 18, 993-1009.

Hogemann et al., 2000, "Improvement of MRI Probes to Allow Efficient Detection of Gene Expression," Bioconjugate Chem. 11:941-946.

Huber et al., 1998, "Fluorescently Detectable Magnetic Resonance Imaging Agents," Bioconjugate Chem. 9:242-249.

Josephson et al., 1999, "High-Efficiency Intracellular Magnetic Labeling with Novel Superparamagnetic-Tat Peptide Conjugates," Bioconj. Chem. 10, 186-191.

Josephson et al., 2001, "Magnetic Nanosensors for the Detection of Oligonucleotide Sequences," Angew Chem Int Ed 40, 3204-3206.

Koenig et al., 1995, "Theory of 1/T1 and 1/T2 NMRD Profiles of Solutions of Magnetic Nanoparticles," Magn Reson Med 34, 227-233.

Kim et al., 2003, "Protective Coating of Superparamagnetic Iron Oxide Nanoparticles," Chem Matter 45: 1617-1627.

Kuhn et al., 2002, "Hybridization of DNA and PNA Molecular Beacons to Single-Stranded and Double-Stranded DNA Targets," J Am Chem Soc. 124, 1097-103.

Le Duc et al., 2001, "Ultrasmall Particle Iron Oxides as Contrast Agents for Magnetic Resonance Spectroscopy: A Dose-Effect Study," J Magn Reson Imaging. 13, 619-26.

Lewin et al., 2000, "Tat Peptide-Derivatized Magnetic Nanoparticles Allow in vivo Tracking and Recovery of Progenitor Cells," Nat Biotechnol. 18, 410-4.

Liu et al., 2002, "Real-Time Monitoring in vitro Transcription Using Molecular Beacons," Analytical Chem., 300:40-45.

Liu et al., 1995, "Self-Assembled Monolayer Coatings on Nanosized Magnetic Particles Using 16-Mercaptohexadecanoic Acid," Langmuir, 11:4617-4622.

Louie et al., 2000, "In vivo Visualization of Gene Expression Using Magnetic Resonance Imaging," Nat Biotechnol. 18:321-325.

Lu et al., 2002, "Modifying the Surface of Superparamagnetic Iron Oxide Nanoparticles through A Sol-Gel Approach," Nano Lett., 2(3):183-186.

Marras et al., 1999, "Multiplex Detection of Single-Nucleotide Variations Using Molecular Beacons," Gen. Analysis, 14:151-156.

Matsuo, 1998, "In situ Visualization of Messenger RNA for Basic Fibroblast Growth Factor in Living Cells," biochimica et Biophysica Acta 1379:178-184.

Mattoussi et al., 2000, "Self-Assembly of CdSe-Zns Quantum Dot Bioconjugates Using an Engineered Recombinant Protein," J. Am. Chem. Soc. 122:12142-12150.

Mirkin et al., 1996, "A DNA-Based Method for Rationally Assembling Nanoparticles into Macroscopic Materials," Nature 382:607-609.

Mitchell et al., 1999, "Programmed Assembly of DNA Functionalized Quantum Dots," J. Am. Chem. Soc. 121:8122-8123.

Mitchell, 2001, "Turning the Spotlight on Cellular Imaging," Nat. Biotech., 19:1013-1017.

Molenaar et al., 2001, "Linear 2' O-Methyl RNA Probes for Visualization of RNA in Living Cells," Nucleic Acids Res. 29 (17):e89:1-10.

Nicewarner-Pena et al., 2001, "Submicrometer Metallic Barcodes," Science, 294:137-141.

Pathak et al., 2001, "Hydroxylated Quantum Dots as Luminescent Probes for in Situ Hybridization," J. Am. Chem. Soc. 123:4103-4104.

Perez et al., 2002, "DNA-Based Magnetic Nanoparticle Assembly Acts as a Magnetic Relaxation Nanoswitch Allowing Screening of DNA-Cleaving Agents," J Am Chem Soc. 124:2856-2857.

Reynolds et al., 2000, "Homogeneous, Nanoparticle-Based Quantitative Colorimetric Detection of Oligonucleotides," J. Am. Chem. Soc. 122:3795-3796.

Santra et al., 2001, "Synthesis and Characterization of Silica-Coated Iron Oxide Nanoparticles in Microemulsion: The Effect of Nonionic Surfactants," Langmuir 17:290-2906.

Shen et al., 1993, "Monocrystalline Iron Oxide Nanocompounds (MION): Physicochemical Properties," Magn Reson Med 29, 599-604.

Sokol et al., 1998, "Real Time Detection of DNA-RNA Hybridization in Living Cells," Proc Natl Acad Sci USA 95:11538-11543.

Storhoff et al., 1999, "Programmed Materials Synthesis with DNA," Chem. Rev. 99:1849-1862.

Tsourkas et al., 2003, "Spectroscopic Features of Dual Fluorescence/Luminscence Resonance Energy-Transfer Molecular Beacons," Anal Chem. 75:3697-3703.

* cited by examiner (A)

(B)

(C)

nanoparticles + phospholipid-PEG mixture in chloroform micellized solution of nanoparticles in water nanoparticle stabilized by PEG-phospholipid coating (a)

(b)

(A)

(B)

A

B

MULTIFUNCTIONAL MAGNETIC NANOPARTICLE PROBES FOR INTRACELLULAR MOLECULAR IMAGING AND MONITORING

CROSS REFERENCE TO RELATED APPLICATIONS

The present invention claims the priority benefit of U.S. Provisional Patent Application Ser. No. 60/421,361 filed Oct. 25, 2002, the entire contents of which are hereby incorporated by reference.

ACKNOWLEDGEMENT OF FEDERAL RESEARCH SUPPORT

This invention was made, at least in part, with funding from the Defense Advanced Research Project Agency (DARPA) of the US Department of Defense (DARPA-AFOSR Grant Number F49620-03-0320 to GB). Accordingly, the United States Government has certain rights in this invention.

FIELD OF THE INVENTION

This invention relates generally to multifunctional magnetic nanoparticle probes that may be used in both optical imaging and deep-tissue magnetic resonance imaging (MRI) and monitoring. More specifically, the present invention relates to magnetic nanoparticles that are coupled with ligand-based in vivo delivery, specific cell targeting, and a molecular probe approach for the detection of target nucleic acids or proteins associated with disease, infection, or injury.

BACKGROUND OF THE INVENTION

Recent advances in nanotechnology and biology include the development of functional nanoparticles (electronic, optical, or magnetic) that are covalently linked to biological molecules such as peptides, proteins, and nucleic acids (See, e.g., Whaley et al., 2000; Bruchez et al., 1998; Chan et al., 1998; Mattoussi et al., 2000; Mitchell et al., 1999; Pathak et al., 2001; Elghanian et al., 1997; Reynolds et al., 2000; Mirkin et al., 1996; Storhoff et al., 1999; Alivisatos et al., 1996; Dubertet et al., 1996). Due to their size-dependent properties and dimensional similarities to biomolecules, these bioconjugates are well suited as contrast agents for in vivo magnetic resonance imaging (MRI)(Josephson et al., 1999; Bulte et al., 1997; Bulte et al., 2001), as luminescent dyes for cellular imaging (Han et al, 2001; Nicewarner-Pena et al., 2001), and as molecular beacons for ultrasensitive optical imaging and detection (Tyagi and Kramer, 1996; Tyagi et al., 1998; Sokol et al., 1998). However, the great potential of magnetic nanoparticles and their bioconjugates as efficient, high throughput and versatile tools for in vivo targeting, sensing and tracking of nucleic acids and proteins has just begun to be exploited (Weissleider, 2001; Shen et al., 1993; Hogemann et al., 2000; Weissleider and Mahmood, 2001).

The ability to monitor and quantify the level of gene expression in living cells in real time can provide important information concerning the production, temporal and spatial processing, localization, and transport of specific mRNA in different conditions. This new type of information could potentially revolutionize medical diagnostics and therapeutics. Technologies currently available for analysis and quantification of gene expression such as real-time RT-PCR, Northern blotting, expressed sequence tag (EST), serial analysis of gene expression (SAGE) and DNA microarrays are powerful tools for in vitro studies; however, they are not capable of quantifying gene expression in living cells. There is a clear need to develop molecular probes that can recognize target mRNA in living cells with high specificity and instantaneously convert such recognition into a measurable signal with a high signal-to-background ratio.

With recent advances in functional genomics and proteomics, there is an urgent need to develop technologies and strategies to detect proteins, multi-protein complexes and protein-protein interactions in vitro. For example, there is a lack of novel labeling reagents in performing in vivo protein expression and interaction studies. There exist few tools that can be used to visualize protein-protein interaction inside cells in deep tissue, and to track the interaction between drug molecules and the associated protein targets. There is virtually no existing method that enables studies of the dynamics of different intra-cellular molecular processes in deep tissue. This is a daunting challenge in that none of the many approaches under development to address these problems have yet demonstrated compelling promise—even as generally effective laboratory-scale small animal models.

Hair-pin oligonucleotide probes have enhanced specificity in detecting single-stranded RNA or DNA targets (Tsourkas et al, 2003). In particular, molecular beacons are a class of fluorescence-quenched hair-pin nucleic acid probes that can be used in a quantitative fashion; these probes fluoresce upon target recognition (i.e., hybridization) with potential signal enhancement of greater than 200 under ideal conditions. Structurally, they are dual-labeled oligonucleotides with a reporter fluorophore at one end and a dark quencher at the opposite end (Tyagi and Kramer; 1996). They are designed to have a target-specific probe sequence positioned centrally between two short self-complementary segments which, in the absence of target, anneal to form a stem-loop hairpin structure that brings the fluorophore in close proximity with the quencher. In this configuration the molecular beacon is in the "dark" state (Bernacchi and Mely, 2001). The hairpin opens upon hybridization with a complementary target, physically separating the fluorophore and quencher. In this configuration the molecular beacon is in the "bright" state. Transition between dark and bright states allows for differentiation between bound and unbound probes and transduces target recognition into a fluorescence signal (Matsuo, 1998; Liu et al., 2002).

The unique target recognition and signal transduction capabilities of molecular beacons have led to their application in many biochemical and biological assays including quantitative PCR (Vogelstein and Kinzler, 1999; Chen and Mulchandani, 2000), protein-DNA interactions (Fang et al., 2000; Li et al., 2000), multiplex genetic analysis (Marras et al., 1999; de Baar et al., 2001), and the detection of mRNA in living cells (Matsuo 1988; Sokol et al., 1998; Molenaar 2001). However, false-positive signals due to protein-beacon interaction and nuclease-induced beacon degradation significantly limit the sensitivity of the in vivo applications (Mitchell, 2001). The thermodynamic and kinetic properties of molecular beacons are dependent on its structure and sequence in complex ways (Bonnet et al. 1999; Kuhn et al., 2002). Moreover, the signal-to-background ratio in target detection is dependent not only on design (length and sequence of the stem and probe) but also on the quality of oligonucleotide synthesis and purification (Goddard et al., 2000; Bonnet et al., 1998) and the assay conditions employed. Although molecular beacons, with the dual FRET (fluorescence resonance energy transfer) design (Tsourkas et al, 2003a) and backbone modifications (Tsourkas at el, 2002b), can be used for sensitive and quantitative detection of mRNA in living cells, they are optical-based probes and therefore cannot be used for deep tissue imaging of RNA expression due to light absorption and scattering.

Compared with micrometer sized magnetic particles and chelates of paramagnetic ions such as gadolinium diethylenetriaminopentaacetic acid (Gd-DTPA), magnetic nanoparticles are much more efficient as relaxation promoters and their effect on the relaxivities of water is measurable even at nanomolar concentrations, as demonstrated theoretically (Koenig and Kellar, 1995) and experimentally (Bulte et al, 1992; Le Duc et al, 2001; Josephson, Perez and Weissleder, 2001; Perez et al, 2002). Specifically, the use of ferromagnetic and superparamagnetic nanoparticles as contrast agents can induce a more than 10 fold increase in proton relaxivities (Coroiu et al, 1999). Based on the enzyme-cleavable contrast agents reported by Meade and coworkers (Huber et al, 1998; Louie et al, 2000), magnetic relaxation by gadolinium atoms is a short-range effect. The presence of a carbohydrate cap (less than 1 nm thick) prevents water molecules from contacting the contrast agent Gd (HP-DO3A). In contrast, superparamagnetic nanoparticles (2-5 nm core size) are often coated by a thick dextran layer (10-20 nm) (Josephson, Perez and Weissleder, 2001), and the encapsulated nanoparticles are highly efficient contrast agents, yielding considerably stronger effects than gadolinium compounds.

Superparamagnetic iron oxide nanoparticles have been extensively studied for different applications including high-density magnetic storage, magnetic nanostructures, catalytic and separation processes (Dyal et al., 2003), contrast agents for magnetic resonance imaging applications (Zhao et al., 2002), functional cell labeling for in vivo tracking of stem cells and tumor progression (Lewin et al., 2000; Bulte et al., 2001), cell and DNA sorting applications (Dressman et al., 2003), drug delivery applications (Lanza et al.), and cellular mechanics studies. Most of these applications require water-soluble, stable, monodispersed, and uniformly sized magnetic nanoparticles. In addition, there is growing interest in applications of magnetic nanoparticles for intracellular molecular imaging. What is needed in the art is to have biocompatible magnetic nanoparticles with a size comparable to the molecular targets (approximately 2-15 nm), with multifunctional ligands. These ligands need to facilitate efficient delivery of nanoparticles, enable specific cell-type recognition, provide suitable biological molecules (antibodies, oligonucleotides etc.) for intracellular targeting, and generate specific MRI contrast via clustering of magnetic nanoparticles or other molecular switch mechanisms.

A variety of coating strategies done both in situ and post-synthesis have been developed for stabilization of magnetic nanoparticles. Post-synthesis coating processes include monolayer ligands (Liu and Xu, 1995; Yee et al., 1999), polymer coatings (Burke et al., 2002; Harris et al., 2003), and silica coatings (Butterworth et al., 2001; Santra et al., 2001; Lu et al., 2002). The monolayer ligand coatings rely on interactions of chemical groups from both the ligand and nanoparticle for effective adsorption or chemisorption of the ligand on the surface. These coatings tend to have limited colloidal stability due to weak steric hindrance in preventing aggregation and have limited opportunity for functionalization. Residual surfactant on the surface of nanoparticles can result in inefficient or incomplete coatings with this approach. The amphiphilic polymer-based or silica-based coating approach often results in multilayer coatings (Lu et al., 2002), making the coating process difficult to control and resulting in a heterogeneous sample, and sometimes in the encapsulation of dimers or trimers of nanoparticles in the same shell (Lu et al., 2002). To improve ease of functionalization and colloidal stability, silica-based coatings are often supplemented with polymers such as polyethylene glycol (Butterworth et al., 2001). In addition to post-synthesis approaches, some in situ coating approaches have been developed, such as the commonly used dextran coatings for MIONs (Kim et al., 2003). These coating processes also lead to multilayer coatings, which can result in a heterogeneous sample. In situ synthesis conditions limit the amount of functionalization that can be achieved.

Recent research has identified several small regions (10-16 amino acids) of proteins called protein transduction domains (PTDs) that possess the ability to traverse biological membranes efficiently in a process termed protein transduction (Lewin et al., 2000; Wadia et al., 2002; Becker-Hapak et al., 2001). Examples of PTDs are HIV-1 Tat, HSV VP22, and ANTP. It was shown that transduction occurs in a receptor- and transporter-independent fashion that appears to target the lipid bilayer directly. Thus, in principle and practice, all cell types appear transducible. Proteins and compounds that are covalently linked to PTDs have proven to be useful in answering specific biological questions where other methods fail. Moreover, PTD fusion proteins have now been introduced into mice and exhibit delivery of active enzyme to all tissues, including across the blood-brain barrier. Recent research shows that magnetic particles as large as 40 nm and liposomes as large as 100 nm can be delivered into cells and tissues.

Traditionally, MRI subjects a tissue to a uniform magnetic field to analyze whether certain features are present or atypical in the subject. MRI uses changes in the angular momentum or "spin" of atomic nuclei of certain elements to show locations of those elements within matter. In particular, a static magnetic field (typically between 0.2 and 4 Tesla) acts on the nuclei of atoms with fractional spin quantum numbers and polarizes them into alignment within the magnetic field. During MRI measurements, radio-frequency pulses of a given resonance energy are applied that flip the nuclear spins and disturb the orientation distribution. The radio-frequency (RF) pulses are in the form of a second, oscillating, RF magnetic field having a particular frequency referred to in the art as a resonant or Larmor frequency. This frequency is equal to the rate that the spins rotate or precess. When the magnetic field is turned off, the nuclei return (relax) to the initial state in a time dependent exponential fashion, thus giving signals which are electronically processed into recordable data. When the signals are spatially differentiated and of sufficient level, the data can be organized and displayed, allowing direct visualization of tissues and organs of a patient. Contrast agents, such as free metal ions, chelates, or insoluble metal compounds have been described for use in enhancing intrinsic contrast in MR imaging. Such metals may include, for example, iron, cobalt, zinc, cadmium, chromium, copper, nickel, manganese, and gadolinium. Magnetic nanoparticles induce a measurable change in the relaxation times $T_1$ and $T_2$ (and $T_2^*$) of surrounding water molecules that can be visualized using MRI. In addition, the coupling or clustering of magnetic nanoparticles generates a different effect on water. These effects of individual or clustered magnetic nanoparticles on water can be differentiated using MRI. However, traditional MRI contrast agents, as well as the use of magnetic nanoparticles with MRI to target cell surface receptors, are not suitable for detecting differential levels of gene expression inside living cells.

Therefore, there is a strong need in the art to provide multifunctional magnetic nanoparticle probes that are suitable for in vivo delivery and that have both signal transduction and target recognition properties. There is also a need for such compositions and methods that can be used for detection of genetic transcription in vivo and in specific cell types Furthermore, there is a need for such compositions and methods that can be used for both optical intra-cellular imaging and deep-tissue molecular imaging using MRI. Moreover, there is a need for such compositions and methods for the rapid and ultrasensitive in vivo detection of diseased cells; virus infection; the rapid detection of internal injury such as traumatic brain injury; and molecular imaging and monitoring of drug activities and therapeutic effects.

SUMMARY OF THE INVENTION

The present invention fulfills in part the need to develop multifunctional magnetic nanoparticle probes for intracellular molecular imaging and monitoring. The novel nanoprobe design and probe/target recognition and binding strategies provide high specificity and sensitivity, and enhanced signal-to-noise ratio in molecular imaging. The peptide-based intracellular delivery of probes and specific cell-type targeting provide the vehicle for efficient internalization of the magnetic nanoparticle probes into selected cells and organs. In addition, the nanoparticle probes of the present invention provide the capability of combining MRI and FRET-based optical imaging, providing for improved spatial resolution and versatility. These innovations and their integration will provide a platform for a new generation of biomagnetic contrast agents for deep tissue molecular imaging and monitoring. The multifunctional magnetic nanoprobes offer a novel transduction mechanism for the in vivo detection of molecular markers for disease, infection, and injury.

Accordingly, the present invention provides improved compositions and methods of use for more sensitive, specific, or rapid nucleic acid or polypeptide detection.

The present invention also provides improved methods for the detection of gene expression associated with a response to external stimuli, e.g. a therapeutic drug candidate. The present invention further provides improved methods for the detection of gene expression, including genetic expression associated with an infection or disease state.

The present invention also provides for the use of such compositions and methods in vivo.

The present invention provides nanoparticle probe compositions for facilitating molecular imaging, comprising: a nucleic acid or polypeptide probe, a delivery ligand, and a detectable moiety, wherein the detectable moiety comprises a magnetic nanoparticle having a biocompatible coating thereon. The present invention also provides that the delivery ligand is a ligand that is capable of facilitating the traverse of a cell membrane. In a preferred embodiment, the magnetic nanoparticle is monocrystalline iron oxide nanoparticle (MION). The present invention also provides that the nanoparticle probe compositions may further comprise a second ligand that is capable of interacting with a molecule located on the outer surface of a particular type of cell or tissue.

The present invention further provides compositions for facilitating signal transduction in molecular imaging, comprising two magnetic nanoparticle probe compositions. The first magnetic nanoparticle probe composition of the present invention comprises a first nucleic acid probe or protein probe, a delivery ligand, and a detectable moiety, wherein the detectable moiety comprises a magnetic nanoparticle having a biocompatible coating thereon. The second magnetic nanoparticle probe composition of the present invention comprises a second nucleic acid probe or protein probe, a delivery ligand, and a detectable moiety, wherein the detectable moiety comprises a magnetic nanoparticle having a biocompatible coating thereon. In certain embodiments, the first and the second magnetic nanoparticle probe compositions comprise a first nucleic acid probe and a second nucleic acid probe, respectively.

The present invention provides that the first nucleic acid probe hybridizes to a first nucleic acid target sequence on a subject nucleic acid; the second nucleic acid probe hybridizes with a second nucleic acid target sequence on the same subject nucleic acid; and the first nucleic acid target sequence and the second nucleic acid target sequence are separated by a number of nucleotides on the subject nucleic acid such that the effect on water relaxation (i.e. a change in the value for $T_1$, $T_2$, or both) from interaction of the first and second magnetic nanoparticles can be detected to determine hybridization of both the first and the second nucleic acid probes. The invention further provides that first magnetic nanoparticle probe, the second magnetic nanoparticle probe, or both further comprise a resonance energy transfer moiety.

In certain other embodiments, the invention provides compositions for facilitating signal transduction in molecular imaging, comprising two magnetic nanoparticle probe compositions wherein the first and the second magnetic nanoparticle probe compositions comprise a first polypeptide probe and a second polypeptide probe, respectively. The present invention provides that such a composition is useful to facilitate the measurement of polypeptide expression, protein interactions, and protein clustering in both in vivo and in vitro systems using magnetic imaging/magnetic spectroscopic measurements. In a preferred embodiment, the present invention provides that the first and the second polypeptide probes bind to a first and a second target sequence on a single subject polypeptide. In another preferred embodiment, the present invention provides that the first polypeptide probe binds to a first subject polypeptide; the second polypeptide probe binds to a second subject polypeptide. When the first subject polypeptide interacts with the second subject polypeptide, the first and second magnetic nanoparticles are brought in close proximity (e.g. 2-50 nm), and the effect on water relaxation (change in $T_1$, $T_2$, or its combination for contrast detection) from interaction of the first and second magnetic nanoparticles can be detected to determine binding of both the first and the second polypeptide probes.

The present invention also provides methods for determining the expression of a subject nucleic acid, comprising introducing the magnetic nanoparticle probe composition of the present invention to a sample suspected of containing the subject nucleic acid; and detecting the presence of the subject nucleic acid by molecular imaging. The present invention provides the detection of the presence of the subject nucleic acid is measured by magnetic resonance imaging (MRI), or the detection may be determined by optical imaging, measuring resonance energy transfer signals.

The present invention also provides methods for determining the expression of a subject polypeptide or interaction of two polypeptides, comprising introducing the magnetic nanoparticle probe composition of the present invention to a sample suspected of containing the subject polypeptide(s); and detecting the presence of the subject polypeptide(s) by molecular imaging. The present invention provides the detection of the presence of the subject polypeptide is measured by magnetic resonance imaging (MRI), or the detection may be determined by optical imaging, measuring resonance energy transfer signals.

The present invention provides novel approaches to engineer biocompatible surface coatings for magnetic nanoparticles using amphiphilic polymers. The biocompatible surface coating of the present invention comprises discrete amphiphilic polymers that can be engineered to control the thickness of the coating and to conjugate multiple ligands on the surface of the coating. These amphiphilic polymer molecules can be engineered either by self-assembled structure or by chelating metal particles in combination with polymers or polymerization, to create the coating for magnetic nanoparticles. This approach can be used to combine different ligand conjugation approaches (for example, proteins, antibodies, peptides, nucleic acid probes, fluorescent dyes and other small molecules). This surface coating may be modified using bifunctional chelating agents or ligands to allow for multiple imaging modalities (e.g. MRI and optical imaging), or it may be used in combination with drug delivery and imaging applications, wherein drug molecules may either be encapsulated in the coated structure or conjugated to the polymer backbone of the coating material, or conjugated directly to the surface of the nanoparticle, or conjugated using multifunctional ligands on the surface of the engineered coating.

The invention further provides methods for producing a magnetic nanoparticle probe composition for facilitating molecular imaging, comprising combining a magnetic nanoparticle with a biocompatible coating; adding a ligand that is capable of facilitating the traverse of a cell membrane; and adding a nucleic acid probe or polypeptide probe. The invention also provides that the methods may comprise the further step of adding a second ligand that is capable of interacting with a molecule located on the outer surface of a particular type of cell or tissue. The invention further provides that these methods may further comprise the step of adding a resonance energy transfer moiety to the magnetic nanoparticle probe composition.

These and other objects, features, and advantages of the present invention will become apparent after a review of the following detailed description of the disclosed embodiments and the appended claims.

BRIEF DESCRIPTION OF THE FIGURES

FIG. 2A shows the binding of two magnetic nanoparticle probe compositions to a subject nucleic acid (i.e. mRNA in this example) via the hybridization of the first and second nucleic acid probes to the complementary first and second target nucleic acid sequence on the subject mRNA molecule. The clustering of the two magnetic nanoparticles as a result of probe-target hybridization induces an altered effect on water relaxation compared with dispersed nanoparticles, leading to a contrast in MR imaging.

FIG. 2B shows the binding of two magnetic nanoparticle probe compositions to a first and second target sequence on a first and second subject proteins, respectively. The interaction of the first and second subject proteins results in the clustering of the two magnetic nanoparticles, which induces an altered effect on water relaxation compared with dispersed nanoparticles, leading to a contrast in MR imaging.

FIG. 2C shows the strategy of using multiple magnetic nanoparticle probe pairs, wherein the nucleic acid probes of each nanoparticle probe bind to the same target mRNA, to increase the signal-to-noise ratio.

FIG. 11A is a graph showing the T2 relaxation times (in ins) of 500 ml cell suspension samples. Column 1 shows values for MDBK cells with MIONs, and Column 2 shows values for the control of MDBK cells alone.

FIG. 11B shows an image of a cross-section of samples from a 3T Siemens MRI system. The first and fourth samples are control samples of media only; the second sample is a control of MDBK cells with media; and the third sample is MdDBK cells with MIONs and media.

DETAILED DESCRIPTION OF THE INVENTION

Figure 1:
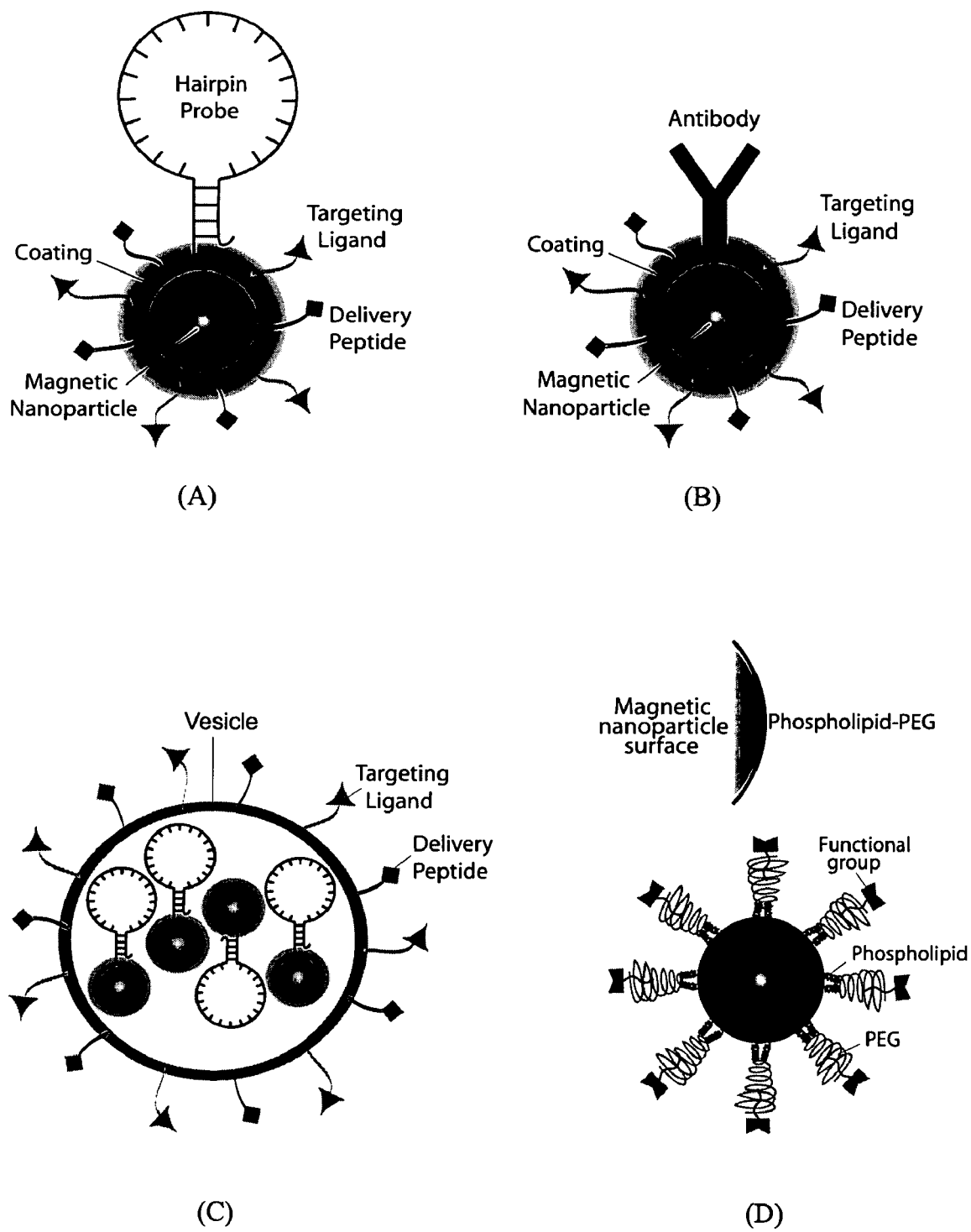
FIG. 1A is a schematic representation showing a single multifunctional magnetic nanoparticle probe consisting of a magnetic nanoparticle, a biocompatible coating, a delivery peptide, a second ligand for targeting, and an oligonucleotide hairpin probe complementary to a specific target nucleic acid sequence.
FIG. 1B is a schematic representation showing a single multifunctional magnetic nanoparticle probe consisting of a magnetic nanoparticle, a biocompatible coating, a delivery peptide, a second ligand for targeting, and an antibody specific for a target polypeptide.
FIG. 1C shows schematically a specific probe composition and in vivo delivery approach in which two or more magnetic nanoparticle probes are wrapped into a vesicle for delivery into deep tissue. In this case, the delivery ligand and second ligand for targeting are conjugated on the vesicle surface instead of on the nanoparticle coating surface.
FIG. 1D is a schematic representation showing one embodiment of the biocompatible coating of magnetic nanoparticle probe, consisting of the phospholipid-linked polyethylene glycol (PEG).

The present invention may be understood more readily by reference to the following detailed description of the preferred embodiments of the invention and the Examples included therein. Before the present compounds, compositions, and methods are disclosed and described, it is to be understood that this invention is not limited to any specific nucleic acid probes, specific nucleic acid targets, specific protein or polypeptide probes, specific polypeptide targets, specific cell types, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a nucleic acid probe" can mean that one or more than one nucleic acid probe can be utilized.

In accordance with the purpose(s) of this invention, as embodied and broadly described herein, the present invention provides, in one aspect, nanoparticle probe compositions for facilitating intracellular molecular imaging, comprising: a targeting probe, a delivery ligand, and a detectable moiety, wherein the detectable moiety comprises a magnetic nanoparticle having a biocompatible coating thereon (FIGS. 1A and 1B) In certain embodiments, the composition further comprises a targeting ligand that is capable of interacting with a molecule on a particular type of cell or tissue.

In certain embodiments of the present invention, the magnetic nanoparticle comprises a metal selected from the group consisting of selected from the group consisting of iron, cobalt, zinc, cadmium, nickel, gadolinium, chromium, copper, manganese, and their oxides. In other embodiments, the magnetic nanoparticle is an alloy with a metal selected from the group consisting of gold, silver, platinum, and copper. The invention further provides that the magnetic nanoparticle may comprise a free metal ion, a metal oxide, a chelate, or an insoluble metal compound. In certain embodiments, the magnetic nanoparticle is selected from the group consisting of $Fe_3O_4$, $Fe_2O_4$, $Fe_xP_ty$, $Co_xP_ty$, $MnFe_xO_y$, $CoFe_xO_y$, $NiFe_xO_y$, $CuFe_xO_y$, $ZnFe_xO_y$, and $CdFe_xO_y$, wherein x and y vary depending on the method of synthesis. In other embodiments, the magnetic nanoparticle further comprises a metal coating selected from the group consisting of gold, silver, iron, cobalt, zinc, cadmium, nickel, gadolinium, chromium, copper, and manganese, and an alloy thereof. In yet other embodiments, the magnetic nanoparticle comprises terbium or europium. In certain preferred embodiments, the magnetic nanoparticle is selected from the group consisting of monocrystalline iron oxide nanoparticle (MION), chelate of gadolinium, and superparamagnetic iron oxide (SPIO). In a preferred embodiment, the magnetic nanoparticle is monocrystalline iron oxide nanoparticle (MION).

In certain preferred embodiments of the present invention, the biocompatible coating is selected from the group consisting of dextran, dendrimers, amphiphilic polymers/bio-polymers (e.g. phospholipids and peptides), polymers, surfactants or chemical compounds with chelating properties for magnetic nanoparticles or high affinity adsorption (e.g. both chemisorption or physical adsorption) on the surface of magnetic nanoparticles, silicon oxide, silica, silica-PEG, mesoporous structures (silica or polymers or their combinations) for encapsulation of nanoparticles, or any other preferred combination of the above. In a further preferred embodiment, the biocompatible coating is an amphiphilic polymer. In an even further preferred embodiment, the biocompatible amphiphilic polymer coating is a phospholipid-PEG coating. In other preferred embodiments phospholipid-PEG may be modified with various bioconjugation reactive groups, including, but not limited to amines, maleimide, thiols, carboxylic acids, NHS esters, and the derivatives of these reactive groups to form phospholipid-PEG-X (wherein X is the modified bioconjugation group(s)). In a further preferred embodiment, mixture of modified phospholipid-PEG molecules with different bioconjugation compatible groups may be used for the coating process. Dextran-coated iron oxide nanoparticles have been approved for clinical human use by the FDA. Extensive studies on the biosafety, biodistribution, and metabolism of these superparamagnetic particles have shown that they are biocompatible and are degraded inside the body. The iron oxide is recycled and becomes raw materials for blood synthesis (hemoglobin). The peptides attached to the particle surface could elicit an immune response if the particles are used in vivo for a long period. However, this is not expected to be a problem when the particles are only used for short-term diagnostics purposes. This problem can be further mitigated by coating the particles with derivatives of polyethylene glycols (PEG), which are known to shield proteins from binding to antibodies.

In certain other preferred embodiments, the coating materials self assemble to form the biocompatible coating. As used herein, a "coating material" refers to a dextran molecule, a dendrimer, an amphiphilic polymer/bio-polymer (e.g. phospholipid, peptide etc.), a polymer, a surfactant, or chemical compound with chelating properties for a magnetic nanoparticle or high affinity for adsorption on a magnetic nanoparticle. In further preferred embodiments, these self-assembled coating materials form a micelle, liposome, or dendrimer shaped structure. In a further preferred embodiment, the coating materials form only a monolayer on the surface of magnetic nanoparticle. In a further preferred embodiment, the monolayer thickness can be engineered by controlling the chain length of the self assembled structure (e.g. the PEG chain length may be controlled for a phosoholipid-PEG biocompatible coating). The present invention also provides that the biocompatible coating can be formed by cross-linking or polymerization of raw coating materials to form a network of molecules on the surface of the magnetic nanoparticle. In a further preferred embodiment, the crosslinking or polymerization process can be controlled by altering the time of the reactions, the amount of raw coating material, the polymer chain length, the temperature, and other processing conditions.

In certain preferred embodiments, the surface of the biocompatibly coated magnetic nanoparticles of the present invention comprise a delivery ligand. As used herein, a "delivery ligand" refers to a molecule that is capable of effectively delivering the magnetic nanoparticle probe across a cell membrane or across both a cell membrane and additional intracellular organelle membrane. In a further preferred embodiment for intracellular delivery, the delivery ligand selected allows for either endocytic or non-endocytic uptake pathways. In a more preferred embodiment, the magnetic nanoparticle probe is delivered using a non-endocytic uptake pathway, using a delivery ligand selected from the group consisting of a protein transduction domain peptide (PTD) and a cell penetrating peptide (CPP). In a further preferred embodiment, the delivery ligand is a TAT peptide. In other embodiments, the delivery ligand may be selected from a group consisting of HIV-1 TAT, HSV VP22, ANTP, poly-Arginine, and Arginine-rich peptides such as W/R, NLS*, AlkCWK18, DiCWK18, transportan, DipaLytic, K16RGD, P1, P2, P3, P3a, P9.3, Plae, Kplae, cKplae, MGP, HA2, LARL46, Hel-11-7, KK, KWK, RWR, and Loligomer. The specific sequences of certain delivery peptides are disclosed in Schwartz and Zhang (2000), and are as follows:

```
                                       (SEQ ID NO: 1)
TAT (with amino acid sequence YGRKKRRQRRR)

(SEQ ID NO: 2)
HSV VP22 DAATATRGRSAASRPTERPRAPARSASRPRRPVE (SEQ ID NO: 3)
ANTP (RQIKIWFQNRRMKWKK)

(SEQ ID NO: 4)
W/R (RRWRRWWRRWWRRWRR)

(SEQ ID NO: 5)
NLS (TPPKKKRKVEDP)

(SEQ ID NO: 6)
AlkCWK₁₈ (CWKKKKKKKKKKKKKKKKK)

(SEQ ID NO: 7)
DiCWK₁₈ (K₁₈WCCWK₁₈)

(SEQ ID NO: 8)
Transportan (GWTLNSAGYLLGKINLKALAALAKKIL)

(SEQ ID NO: 9)
DipaLytic (GLFEALEELWEAK)
```

```
-continued
                                       (SEQ ID NO: 10)
K₁₆RGD (K₁₆GGCRGDMFGCAK₁₆RGD)

(SEQ ID NO: 11)
P1 (K₁₆GGCMFGCGG)

(SEQ ID NO: 12)
P2 (K₁₆ICRRARGDNPDDRCT)

(SEQ ID NO: 13)
P3 (KKWKMRRNQFWVKVQRbAK(B)bA)

(SEQ ID NO: 14)
P3a (VAYISRGGVSTYYSDTVKGRFTRQKYNKRA)

(SEQ ID NO: 15)
P9.3 (IGRIDPANGKTKYAPKFQDKATRSNYYGNSPS)

(SEQ ID NO: 16)
Plae (PLAEIDGIELTY)

(SEQ ID NO: 17)
Kplae (K₁₆GGPLAEIDGIELGA)

(SEQ ID NO: 18)
cKplae (K₁₆GGPLAEIDGIELCA)

(SEQ ID NO: 19)
MGP (GALFLGFLGGAAGSTMGAWSQPKSKRKV)

(SEQ ID NO: 20)
HA2 (WEAK(LAKA)₂LAKH(LAKA)₂LKAC)

(SEQ ID NO: 21)
LARL4₆ ((LARL)₆-NH-CH₃)

(SEQ ID NO: 22)
Hel-11-7 (KLLKLLLKLWLKLLKLLL)

(SEQ ID NO: 23)
KK ((KKKK)₂ GGC)

(SEQ ID NO: 24)
KWK ((KWKK)₂ GCC)

(SEQ ID NO: 25)
RWR ((RWRR)₂ GGC)

(SEQ ID NO: 26)
Loligomer ((K9K2)(K4)(K8)GGKKKKK-NLS).

wherein NLS consists of the NLS sequence
disclosed in this paragraph as SEQ ID NO:5.
```

In certain other embodiments, the magnetic nanoparticle probe may be delivered using endocytic routes. In a further preferred embodiment, the endocytic route may require a ligand which has both targeting and delivery functions e.g. folic acid for targeting folic acid receptors on cancer cells. In certain other preferred embodiments, the endocytic route targeted delivery may be supplemented with endosomal disruption agents or agents for early release of probes from endosomes such as pH sensitive polymeric materials or ligands selected from certain viruses. In certain other preferred embodiments, the probe may be delivered using a transfection agent, which may be lipid-, polymer-, dendrimer-based or their combinations, or their combinations with themselves or with other ligands such as peptides, proteins, and small molecules.

In certain embodiments, the coated magnetic nanoparticles are further modified with a second ligand. The present invention provides that the second ligand is a molecule that is capable of interacting with a molecule on a particular type of cell or tissue. In a preferred embodiment, the second ligand is selected from a group consisting of a polypeptide, a peptide, an antibody, an antibody fragment, an oligonucleotide-based aptamer with recognition pockets, and a small molecule that binds to a specific cell surface receptor or polypeptide on the outer surface of the cell wherein the cell surface receptor or polypeptide is specific to that cell type. The present invention provides that the second ligand has a function to target a specific tissue, cell type, or disease-specific marker. As used herein, the term "disease-specific marker" refers to the increased expression of certain proteins on the cell surface of a diseased cell; the expression of foreign protein (e.g. viral proteins) expressed on cell surface of the infected cell; and the expression of markers associated with specific pathophysiological states such as angiogenesis, which may be associated with tumor tissue. In certain embodiments this targeting function may increase the efficiency of intracellular delivery. In a further preferred embodiment, the magnetic nanoparticles probe has ligands with both targeting and delivery functions. As used herein, the term "targeting function" refers to the ability of a molecule to specifically interact with a molecule on a particular type of tissue or cell, including a cancerous or diseased cell. As also used herein, the term "delivery function" refers to the ability of a molecule to effectively deliver the magnetic nanoparticle probe across a cell membrane or across both a cell membrane and an additional intracellular organelle membrane In one embodiment, the targeting and delivery function may be achieved by the use of a single ligand or by using two or more ligands attached to the biocompatible coating of the magnetic nanoparticle probe. In certain embodiments, the ligands may be removed from the magnetic nanoparticle probe after intracellular delivery of the probe. This removal process may be based, for example, on reduction, oxidation, light (including UV, visible, infrared) associated cleavage, proteolytic cleavage, and enzymatic reactions.

In certain other preferred embodiment the ligand attached coated magnetic nanoparticles are further modified with reporter probe molecules for multi-modality imaging abilities such as fluorescent dyes, radioisotopes, luminescent molecules/bioluminescent polypeptides, or other biomolecules. In certain other embodiments, drug molecules may also be encapsulated, conjugated, or attached to the coating either on the surface or at its backbone to monitor the drug bioavailability, delivery, and lifetime of the drug, along with the MRI and optical imaging applications.

In a preferred embodiment central to this invention, the targeting probe comprises a nucleic acid probe attached to the surface of the coated magnetic nanoparticle. The attachment of the nucleic acid probe to the surface of the coated magnetic nanoparticle may involve a covalent attachment or high affinity adsorption/binding using non-covalent attachment through other biomolecules such as peptides or proteins attached to the magnetic nanoparticle coating surface, for example, utilizing a streptavidin-biotin linkage. In one preferred embodiment, the nucleic acid probe is covalently attached to the surface of the probe through chemical modifications to generate a functional group either at the 3' end, the 5' end, or anywhere in the sequence of the probe (i.e. an internal modification of nucleic acid probe). In a further preferred embodiment, the coated magnetic nanoparticle probe comprising the nucleic acid probe is further modified with a ligand or ligands to effectively target and deliver the magnetic nanoparticle probe. In a further preferred embodiment the coated magnetic nanoparticle probe is also modified with a fluorescent reporter molecule, a radioisotope reporter molecule, or both.

Figure 2:
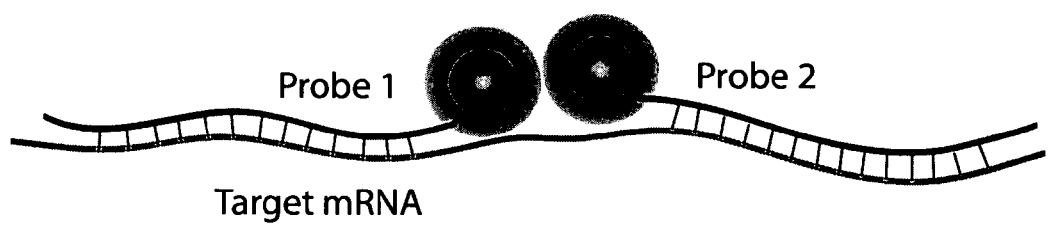
FIG. 2 shows the signal transduction mechanisms.
Figure 2:
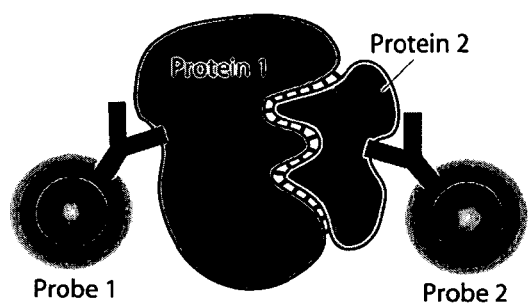
Figure 2:
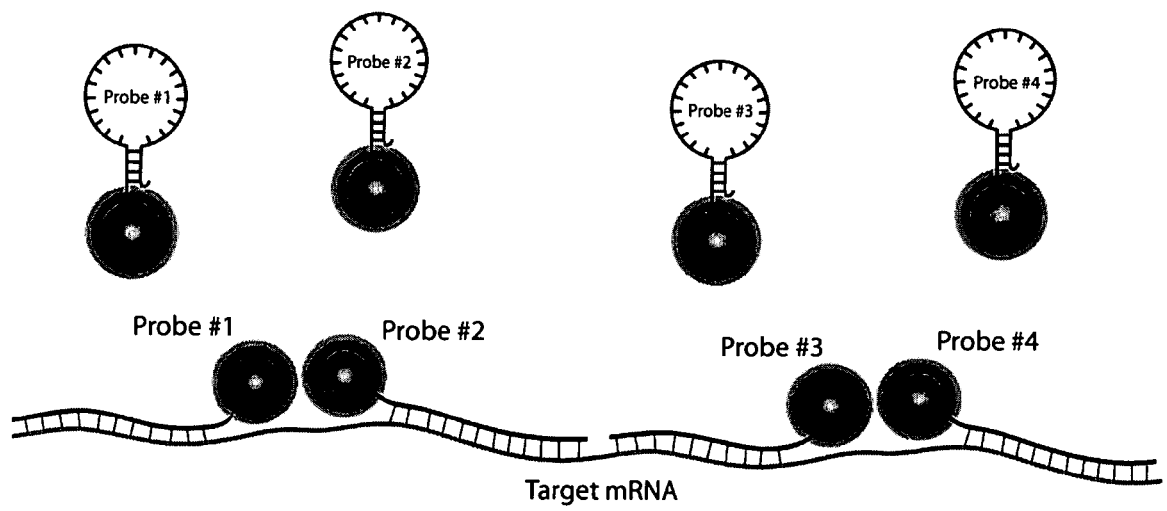

In a preferred embodiment, the nucleic acid probe selected for attachment to the magnetic nanoparticle probe is either fully complementary or partially complementary to a target nucleic acid sequence on a subject nucleic acid. In a further preferred embodiment, two or more magnetic nanoparticle probes comprising a nucleic acid probe are used. The two or more target nucleic acid sequences are selected in a way such that when the two or more nucleic acid probes hybridize to the respective target nucleic acid sequence, the two or more magnetic particles are brought in close proximity (FIGS. 2A and 2C). In a preferred embodiment the nucleic acid probes hybridizes to target sequence in a complementary fashion to form a duplex. In certain embodiments the nucleic acid probes may be designed to form triplexes or other secondary structures required based on mRNA sequence requirement to create contrast based on magnetic relaxation. In a further preferred embodiment, the distance between the two magnetic particles may be chosen based on the design of the target nucleic acid sequences, the nucleic acid probes, and the secondary/tertiary structure of the target nucleic acid sequences such that a significant shift in magnetic relaxation (T1 and/or T2 relaxation time) is achieved as compared to single magnetic nanoparticle probe hybridized to a target sequence. In certain embodiments, multiple pairs of magnetic particles with nucleic acid probes are used, as illustrated in FIG. 2C, wherein the nucleic acid probes of each of the magnetic nanoparticle probes hybridize with a single subject target nucleic acid to enhance the signal-to-noise ratio and to generate a significant MR contrast.

In certain embodiments, the present invention further provides compositions for facilitating intracellular molecular imaging, comprising at least two magnetic nanoparticle probe compositions. The first magnetic nanoparticle probe composition of the present invention comprises a first targeting probe, a delivery ligand, and a detectable moiety, wherein the detectable moiety comprises a magnetic nanoparticle having a biocompatible coating thereon. The second magnetic nanoparticle probe composition of the present invention comprises a second targeting probe and a detectable moiety, wherein the detectable moiety comprises a magnetic nanoparticle having a biocompatible coating thereon. In one embodiment, the first and second targeting probes are nucleic acid probes. The present invention provides that the first nucleic acid probe hybridizes to a first nucleic acid target sequence on a subject nucleic acid; the second nucleic acid probe hybridizes with a second nucleic acid target sequence on the subject nucleic acid; and the first nucleic acid target sequence and the second nucleic acid target sequence are separated by a number of nucleotides on the subject nucleic acid such that an effect on water relaxation from interaction between the first and second magnetic nanoparticles can be detected to determine hybridization of both the first and second nucleic acid probes.

In a preferred embodiment for cellular or in vivo molecular imaging, mRNA is the subject nucleic acid. In a further preferred embodiment, the subject mRNA has a characteristic up-regulation or down-regulation that is associated with a disease-specific or injury-specific condition; the subject mRNA is a foreign mRNA such as a viral or bacterial mRNA; or the subject mRNA is specific to a particular cell phenotype, stem cell lineage, or cell differentiation. In a preferred embodiment, the nucleic acid probe will form a hairpin structure, wherein the hairpin oligonucleotide probes have different loop lengths and stem lengths, depending on the specific target mRNA and requirements of probe/target hybridization specificity, sensitivity, and signal-to-noise ratio. In a further preferred design the hairpin shape (length of stem and loop domain) of the nucleic acid probe may be designed based on thermodynamic, kinetic, and its combination principles to increase specificity of the probe and reduce nonspecific interactions of the nucleic acid probe nucleotides. In certain other embodiments, the nucleic acid probe may be chosen to have a linear or random structure.

In one embodiment of the present invention, the first or second nucleic acid probes comprise 10 to 90 nucleotides. In a preferred embodiment, the first or second nucleic acid probes comprise 10 to 40 nucleotides. Even more preferred, the first or second nucleic acid probes comprise 15 to 30 nucleotides. More preferred, the first or second nucleic acid probes comprise 20 to 25 nucleotides.

In various embodiments, the first nucleic acid target sequence and the second nucleic acid target sequence are separated by 10 to 150 nucleotides, or separated by 10, 20, 30, 40, 50, 60, 70, 80, 90, 100, 110, 120, 130, 140 or 150 nucleotides. As discussed below, the preferred number of separating nucleotides will vary depending upon the size of the nanoparticles and the size of the biocompatible coating, and can be routinely determined by one of skill in the art in view of the present disclosure.

In other preferred embodiments of the present invention, the chemistry of the nucleic acid probe(s) are chosen to be resistant to nuclease and proteolytic activity, with high affinity for the target sequence with low affinity for nonspecific binding. For example, a nucleic acid probe of the present invention can be chemically synthesized using naturally occurring nucleotides or variously modified nucleotides designed to increase the biological stability of the molecules or to increase the physical stability of the duplex formed between the complimentary nucleic acids, e.g., phosphorothioate derivatives and acridine substituted nucleotides can be used. Preferred examples of classes of modified nucleotides which can be used to generate the nucleic acid probes are a 2'-O-methyl nucleotide and a peptide nucleic acid backbone. Additional examples of modified nucleotides which can be used to generate the nucleic acid probes include, for example, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the nucleic acid probe of the present invention comprises at least one modified sugar moiety selected from the group including but not limited to arabinose, 2-fluoroarabinose, xylulose, and hexose. In yet another embodiment, the nucleic acid probe of the present invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. As stated above, a preferred example of a modified nucleotide which can be used to generate the nucleic acid probes is a 2'-O-methyl nucleotide. In certain embodiments, regular nucleic acid probes without any modification may be used to target the mRNA of interest.

The present invention provides that the first nucleic acid probe, the second nucleic acid probe, or both may have a linear, randomly coiled, or stem-loop structure when not hybridized to the first or the second nucleic acid target sequence. In a preferred embodiment, the nucleic acid probes form a stem-loop structure when not hybridized to the respective target sequence. In another embodiment the first or second magnetic nanoparticle probe further incorporates a resonance energy transfer donor or acceptor moiety on the biocompatible coating, such that a resonance energy transfer signal from interaction between the donor moiety and the acceptor moiety on the first and second magnetic nanoparticle probes can be detected to determine the hybridization of the first and the second nucleic acid probes. In a preferred embodiment, the resonance energy transfer signal is due to fluorescence resonance energy transfer.

In theory, the oligonucleotides on the nanoparticle surface could generate an antisense effect by hybridizing with mRNA molecules inside cells, but this effect should be minor because (a) the oligonucleotide probes we will use are very short (14-24 bases) and (b) the nanoprobes are only used for short-term diagnosis of diseases (such as infection) and injuries. Specifically, as far as diagnosis is concerned, the binding between oligonucleotide probes and specific mRNAs in the diseased or injured cells should not have a large detrimental effect on the health of the patient. If the nanoprobes are being delivered into normal cells as well, the oligonucleotide may not have any effect provided there is no target mRNA inside the normal cell (such as mutations). The antisense effect of the magnetic nanoparticle probe could be used as a therapeutic or monitoring agent.

In additional embodiments, the invention provides methods for detecting a subject nucleic acid, comprising combining the composition described herein with a sample suspected of containing a subject nucleic acid, and detecting hybridization by differential MRI contrast to determine the presence or absence, and/or the expression level of the subject nucleic acid in the sample in vitro or in vivo. As used herein, the term "MRI contrast" refers to an effect on the water relaxation in a particular sample. In some preferred embodiments, the methods can be performed in vivo. Therefore, in a preferred embodiment of this method, the sample contains a living cell, a living animal, or a living human being. The invention provides that the methods may be performed with samples comprising living tissues and cells that are taken out of the body, or that remain in situ.

The methods of the present invention further include detection of changes in the levels of expression of a nucleic acid target, or in RNA transcript, such that alterations of gene expression can be monitored as a result of the dose-dependent cellular response to external stimuli, such as drug molecules, hormones, growth factors, temperature, shear flow, or microgravity, for example. The invention further provides that the compositions can be used to visualize, i.e., through MRI, fluorescence, or luminescence, the location and relative amount of gene expression in tissues and cells. The invention also provides that the compositions can be used to permit the detection of a subject nucleic acid, indicating the presence of a virus, a diseased cell, or a traumatic injury.

In diagnostic or prognostic detection methods, the subject nucleic acid can comprise a genetic point mutation, deletion, or insertion relative to a naturally occurring or control nucleic acid. Such screening methods can permit the detection of the subject nucleic acid indicating the presence of a genetically associated disease, such as certain cancers, in the sample. There are many well-known examples of genetic mutations already in the art that are indicative of a disease state. The methods include the detection of nucleic acids comprising K-ras, survivin, p53, p16, DPC4, or BRCA2. Furthermore, the methods can be used to detect the amount of a subject nucleic acid being produced by an organism for purposes other than diagnosis or prognosis of a disease or condition. Resonance energy transfer detections of the present invention can be performed with the assistance of single- or multiple-photon microscopy, time-resolved fluorescence microscopy or fluorescence endoscopy, as detailed below.

One embodiment of the present invention provides magnetic nanoparticle probe compositions comprising nucleic acid probes, and methods that measure a resonance energy transfer, for example, a fluorescent signal due to FRET or LRET as a result of two different nucleic acid probes hybridizing to the same target nucleic acid of interest. This approach utilizes a pair of magnetic nanoparticle probes with different nucleic acid probes that hybridize to a single subject nucleic acid. One magnetic nanoparticle probe further comprises a donor fluorophore on the surface of its biocompatible coating, and the second magnetic nanoparticle probe comprises an acceptor fluorophore on the surface of its biocompatible coating (FIG. 7B). Probe sequences are chosen such that the magnetic nanoparticle probes hybridize adjacent to each other on a single nucleic acid target in a way that their respective fluorophores have FRET or LRET. Emission from the acceptor fluorophore serves as a positive signal in the FRET/LRET based optical detection assay. This will allow sensitive detection of a target nucleic acid inside cells in shallow tissue with higher spatial resolution (approximately 200 mm) as compared to the spatial resolution of MRI (approximately 0.1 mm).

The magnetic nanoparticle probes of the invention utilize the principle of resonance energy transfer between a donor moiety and an acceptor moiety. In a preferred embodiment, the resonance energy transfer is fluorescence resonance energy transfer (FRET), in which the first and second magnetic nanoparticle probes are labeled with donor and acceptor moieties on the surface of their biocompatible coatings, respectively, wherein the donor moiety is a fluorophore and the acceptor moiety may be a fluorophore, such that fluorescent energy emitted by the donor moiety is absorbed by the acceptor moiety when both probes are hybridized to the first and second target sequences respectively on the same nucleic acid subject. In one embodiment of the present invention, the acceptor moiety is a fluorophore that releases the energy absorbed from the donor at a different wavelength; the emissions of the acceptor may then be measured to assess the progress of the hybridization reaction.

In preferred embodiments, the resonance energy signals are due to fluorescence resonance energy transfer (FRET) or luminescence resonance energy transfer (LRET). In embodiments wherein the resonance energy transfer signal is due to fluorescence resonance energy transfer, the donor moiety can be for example a Cy3 fluorophore. In embodiments wherein the resonance energy transfer signal is due to fluorescence resonance energy transfer, the acceptor moieties can be a Cy5 fluorophore. Additional examples of FRET donor and acceptor moieties useful in the present invention are provided below. If acceptor and donor fluorophores are well matched, excitation of the donor can be achieved at a wavelength that has little or no capacity to excite the acceptor; excitation of the acceptor will therefore only occur if both nucleic acid probes are hybridized to the same target nucleic acid and FRET occurs.

In other embodiments, the resonance energy transfer signal is due to luminescence resonance energy transfer (LRET) and the donor moiety is a lanthanide chelate. In some preferred embodiments where the resonance energy signal is due to LRET, the donor moiety can be Europium or Terbium. Furthermore, in some embodiments where the resonance energy signal is due to LRET, the donor moiety can be a lanthanide chelate such as DTPA-cytosine, DTPA-cs124, BCPDA, BHHCT, Isocyanato-EDTA, Quantum Dye, or W1024 and the acceptor moiety can be Cy-3, ROX or Texas Red. In some embodiments, due to the range of effective resonance energy transfer of the lanthanide chelate, multiple acceptor moieties may be employed. The donor moiety can be a lanthanide chelate and the acceptor moiety can be a phycobiliprotein. In certain embodiments, the phycobiliprotein is Red Phycoerythrin (RPE), Blue Phycoerythrin (BPE), or Allophycocyanin (APC). Additional examples of LRET donor and acceptor moieties useful in the present invention are provided below.

Magnetic nanoparticle probes of the present invention may be labeled with donor and acceptor moieties on the biocompatible coating surface so that the resulting fluorescence or luminescence resonance energy transfer signal may be detected upon probe/target hybridization (FIG. 7B), in addition to the MRI signal. In a specific embodiment, the following donor and acceptor pairs are used: a luminescent lanthanide chelate, e.g., terbium chelate or lanthanide chelate, is used as the donor, and an organic dye such as fluorescein, rhodamine or Cy5, is used as the acceptor. Preferably, terbium is used as a donor and fluorescein or rhodamine as an acceptor, or europium is used as a donor and Cy5 as an acceptor.

In contrast to using two linear oligonucleotide probes attached to two different magnetic nanoparticles, nucleic acid probes with a stem-loop hairpin structure offer further reduction in background fluorescence as well as enhanced specificity, which is helpful particularly when detection of allelic variants or point mutations is desired (Bonnet et al., 1999; Tsourkas et al., 2002a).

The nucleic acids of the present invention may be substantially isolated or alternatively unpurified. An "isolated" or "purified" nucleic acid is one that is substantially separated from other nucleic acid molecules that are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule can be substantially free of other cellular material, or culture medium when produced by recombinant techniques, or chemical precursors or other chemicals when chemically synthesized. (see, Sambrook et al. 1989, *Molecular Cloning: A Laboratory Manual. 2nd, ed., Cold Spring Harbor Laboratory*, Cold Spring Harbor Laboratory Press, Cold Spring Harbor, N.Y.).

The probe typically comprises substantially purified nucleic acid. The nucleic acid probe typically comprises a region of nucleotide sequence that hybridizes to at least about 10, 11, 12, 13, 14, 15, 16, 17, 18, 19, 20, 21, 22, 23, 24, 25, 26, 27, 28, 29, 30, 35, 40, 45, 50, 60, 70, 80, or 90 consecutive nucleotides of a target nucleic acid. The target nucleic acid can be a sense strand of one of the target nucleic acid sequences, an anti-sense sequence, or naturally occurring mutants thereof. Preferably, the nucleic acid target is an mRNA.

Probes based on the nucleotide sequences can be used to detect or amplify transcripts or genomic sequences encoding the same or homologous proteins. In other embodiments, the probe further comprises a label group attached thereto, e.g., the label group can be a radioisotope, an enzyme, or an enzyme co-factor. Such probes can be used as a part of a genomic marker test kit for identifying cells which express a particular protein, such as by measuring a level of the protein-encoding nucleic acid in a sample of cells, e.g., detecting the target nucleic acid mRNA levels or determining whether the gene encoding the mRNA has been mutated or deleted.

In an additional preferred embodiment, an isolated nucleic acid molecule of the invention comprises a nucleic acid probe sequence that hybridizes, e.g., hybridizes under stringent conditions, to a target nucleotide sequence of interest. These hybridization conditions include washing with a solution having a salt concentration of about 0.02 molar at pH 7 at about 60° C. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989) 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. As used herein, a "naturally-occurring" nucleic acid molecule refers to an RNA or DNA molecule having a nucleotide sequence that occurs in nature (e.g., encodes a natural protein).

The nucleic acid probes of the invention can be DNA or RNA or chimeric mixtures or derivatives or modified versions thereof, so long as it is still capable of hybridizing to the desired target nucleic acid. In addition to being labeled with a resonance energy transfer moiety, the nucleic acid sequence can be modified at the base moiety, sugar moiety, or phosphate backbone, and may include other appending groups or labels, so long as it is still capable of priming the desired amplification reaction, or functioning as a blocking oligonucleotide, as the case may be.

Nucleic acid probes of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Suitable moieties that can be selected as donor or acceptors in FRET pairs are set forth below:

4-acetamido-4'-isothiocyanatostilbene-2,2'disulfonic Acid
Acridine and Derivatives
   acridine
   acridine isothiocyanate
   5-(2'-aminoethyl)aminonaphthalene-1-sulfonic acid (EDANS)
   4-amino-N-[3-vinylsulfonyl)phenyl]naphthalimide-3, 5disulfonate(LuciferYellow VS)
   N-(4-anilino-1-naphthyl)maleimide
   Anthranilamide
   Brilliant Yellow coumarin and derivatives:
   coumarin
   7-amino-4-methylcoumarin (AMC, Coumarin 120)
   7-amino-4-trifluoromethylcoumarin (Coumarin 151)
   cyanosine
   4'-6-diaminidino-2-phenylindole (DAPI)
   5',5"-dibromopyrogallol-sulfonephthalein (Bromopyrogallol Red)
   7-diethylamino-3-(4'-isothiocyanatophenyl)-4-methylcoumarin diethylenetriamine pentaacetate
   4-(4'-diisothiocyanatodihydro-stilbene-2,2'-disulfonic acid
   4,4'-diisothiocyanatostilbene-2,2'-disulfonic acid
   5-[dimethylamino]naphthalene-1-sulfonyl chloride (DNS, dansyl chloride)
   4-(4'-dimethylaminophenylazo)benzoic acid (DABCYL)
   4-dimethylaminophenylazophenyl-4'-isothiocyanate (DABITC)

Eosin and Derivatives:
   eosin
   eosin isothiocyanate

Erythrosin and Derivatives:
   erythrosin B
   erythrosin isothiocyanate
   ethidium Fluorescein and Derivatives:
   5-carboxyfluorescein (FAM)
   5-(4,6-dichlorotriazin-2-yl)aminofluorescein (DTAF)
   2'7'-dimethoxy-4'5'-dichloro-6-carboxyfluorescein (JOE)
   fluorescein
   fluorescein isothiocyanate
   QFITC (XRITC)
   fluorescamine
   IR144
   IR1446
   Malachite Green isothiocyanate
   4-methylumbelliferone
   ortho cresolphthalein
   nitrotyrosine
   pararosaniline
   Phenol Red
   B-phycoerythrin
   o-phthaldialdehyde Pyrene and Derivatives:
   pyrene
   pyrene butyrate
   succinimidyl 1-pyrene butyrate
   Reactive Red 4 (Cibacron® Brilliant Red 3B-A)

Rhodamine and Derivatives:
   6-carboxy-X-rhodamine (ROX)
   6-carboxyrhodamine (R6G)
   lissamine rhodamine B sulfonyl chloride
   rhodamine (Rhod)
   rhodamine B
   rhodamine 123
   rhodamine X isothiocyanate
   sulforhodamine B sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives
Alexa Derivatives
Alexa-350
Alexa-488
Alexa-547
Alexa-647

In yet another embodiment, the magnetic nanoparticle probes of the invention may be further labeled on the biocompatible coating surface with any other art-known detectable marker, including a radioisotope, such as $^{32}P$, $^{35}S$, $^{3}H$, and the like; a fluorescent dye; an organic bead with fluorescent or luminescent characteristics; an inorganic bead with fluorescent or luminescent characteristics; and enzymatic markers that produce detectable signals when a particular chemical reaction is conducted, such as alkaline phosphatase or horseradish peroxidase. Such enzymatic markers are preferably heat stable, so as to survive the denaturing steps of the amplification process. Magnetic nanoparticle probes may also be indirectly labeled on the biocompatible coating surface by incorporating a nucleotide linked covalently to a hapten or to a molecule such as biotin, to which a labeled avidin molecule may be bound, or digoxygenin, to which a labeled anti-digoxygenin antibody may be bound.

The magnetic nanoparticle probes of the invention have use in nucleic acid and polypeptide detection. Accordingly, the magnetic nanoparticle probes of the invention can be used in methods of diagnosis, wherein a sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The subject nucleic acid can be genomic or cDNA or mRNA or synthetic, human or animal, or of a microorganism, etc.

The present invention also provides methods for determining the expression of a subject nucleic acid, comprising introducing the magnetic nanoparticle probe composition of the present invention to a sample suspected of containing the subject nucleic acid; and detecting the presence of the subject nucleic acid by intracellular molecular imaging. The present invention provides the detection of the presence of the subject nucleic acid is measured by magnetic resonance imaging (MRI), or the detection may be determined by optical imaging, measuring resonance energy transfer signals. In one embodiment, the methods are performed in vivo. In a preferred embodiment, the sample contains a living cell, a living animal, and/or a patient. In certain embodiments, the composition is introduced into may be delivered into shallow or deep tissue of the patient by injection, inhalation, intranasal administration, oral administration, sublingual administration, buccal administration, topical administration, local delivery to tissue, or direct delivery into blood stream. In a further preferred embodiment, the composition is introduced by subcutaneous injection, intravenous injection, intradermal injection, intramuscular injection, or microinjection. Further in animal systems, probe may be delivered using tail vein injections.

In certain embodiments as illustrated in FIG. 1C, it may be significantly advantageous to encapsulate the single probe or multiple probes for single or multiple intracellular targets in a single vesicle. In certain preferred embodiments, multiple magnetic nanoparticle probes with multiple target sequences are designed to target delivery and imaging for disease detection and drug monitoring using the vesicle design. In certain preferred embodiments for single or multiple magnetic nanoparticle probes, this encapsulation embodiment may allow us to effectively monitor multiple targets simultaneously either using a single imaging technique or some combination of multimodality imaging (any combination of MRI, nuclear imaging, and optical imaging); to improve the stability of the magnetic nanoparticle probe compositions; to reduce non-specific interactions of the magnetic nanoparticle probe compositions in the blood stream; and to increase the life time of circulation of our magnetic nanoparticle probe compositions. The inclusion of more than one delivery ligand and/or more than one targeting ligand on the surface of such vesicle-encapsulated magnetic nanoparticle probe composition may increase the effective targeting of tissues, diseased cells, and infected cells, and will allow the effective control of the concentration of delivered magnetic nanoparticle probes which many improve significantly the signal to noise ratio. In certain embodiments, such encapsulation may also facilitate the delivery of magnetic nanoparticle probe compositions for multimodality imaging applications. Specifically, a magnetic nanoparticle probe may have multimodality imaging abilities, or the vesicle surface may also be modified to include such abilities.

As illustrated in FIG. 1C, in other embodiment of the above design of magnetic nanoparticle probes, it may be advantageous to encapsulate the entire magnetic nanoparticle probe or multiple magnetic nanoparticle probes, both nucleic acid and protein targeting probes in a vesicle. As used herein, the term "vesicle" refers to a biocompatible coating selected from the group consisting of a lipid bilayer, a mesoporous solid (e.g. mesoporous silica, polymer, or any combination thereof) or dendrimers. The vesicles of the present invention may be targeted to a specific type of cell or tissue using a combination of a delivery ligand and a targeting ligand as described above. In a further preferred embodiment the in vivo delivery of the probe-containing vesicles do not illicit a significant immune response. This effect may be provided by a biocompatible coating (e.g. PEG-based coating) on the outer exposed surface of the vesicle. In a further preferred embodiment, the capsule material is biodegradable, and fast release of probes from the capsule can be achieved due to reduction or light activable decay (UV, visible, or infrared light) of the capsule material. In certain embodiments some drug molecules may also be encapsulated along with the probes to allow for monitoring of the drug activities and the effect of treatment.

In one embodiment the inventors provide a useful screening tool for drug discovery where a rapid specific and sensitive assay can detect in vivo changes in the expansion role of protein transcripts of interest, either at a steady state or in response to the administration of drug candidates. In another embodiment that can be used in the diagnosis or prognosis of a disease or disorder, the target sequence is a naturally occurring or wild type human genomic or RNA or cDNA sequence, mutation of which is implicated in the presence of a human disease or disorder, or alternatively, the target sequence can be the mutated sequence. In such an embodiment, optionally, the amplification reaction can be repeated for the same sample with different sets of probes that amplify, respectively, the naturally occurring sequence or the mutated version. By way of example, the mutation can be an insertion, substitution, and/or deletion of one or more nucleotides, or a translocation.

In one embodiment, the detection of the subject nucleic acid indicates the presence of a cancer in the sample. In a preferred embodiment, the subject nucleic acid comprises K-ras, survivin, p53, p16, DPC4, or BRCA2. In other embodiments, the detection of the subject nucleic acid indicates an alteration of the expression pattern of the subject nucleic acid in response to an external stimulus or indicates the presence of a virus in the sample.

The invention further provides methods for producing a magnetic nanoparticle probe composition for facilitating molecular imaging, comprising combining a magnetic nanoparticle with a biocompatible coating; adding a peptide ligand that is capable of facilitating the traverse of a cell membrane; and adding a nucleic acid probe. In some embodiments, the magnetic nanoparticle probe composition further comprises the step of adding a second ligand for targeting the composition to a particular type of cell or tissue.

In one embodiment of the present invention, the nucleic acid probe hybridizes to a nucleic acid target sequence on a subject nucleic acid and forms a stem-loop structure when not bound to the nucleic acid target sequence. In another embodiment, the nucleic acid probe hybridizes to a nucleic acid target sequence on a subject nucleic acid and has a linear or randomly coiled structure when not bound to the nucleic acid target sequence. In yet another embodiment, the nucleic acid probe comprises a modification of the nucleic acid backbone. The invention further provides that these methods may comprise the use of a nucleic acid probe that incorporates a resonance energy transfer moiety.

In certain other embodiments of the present invention, several magnetic nanoprobes (4-6) will be hybridized on the same target. This could lead to an increased sensitivity and signal-to-noise ratio. In other embodiments, each magnetic nanoprobe can comprise a hairpin probe and two magnetic nanoparticles at the end of the stem.

In addition to MRI-based contrast generation based on the clustering of two or more magnetic nanoparticles as a result of hybridization of nucleic acid probes, the same contrast generation strategies can be developed to detect polypeptide expression or protein-protein interactions between known pairs of proteins both in biochemical, cellular and in vivo molecular imaging assays. In a preferred embodiment, a nanoparticle probe composition comprises a first magnetic nanoparticle probe composition comprising a first polypeptide probe, a delivery ligand, and a detectable moiety; and a second magnetic nanoparticle probe composition comprising a second polypeptide probe, a delivery ligand, and a detectable moiety, wherein the detectable moiety comprises a magnetic nanoparticle having a biocompatible coating thereon; wherein the first polypeptide probe hybridizes to a first target sequence and the second polypeptide probe hybridizes with a second target sequence; and wherein an effect on water relaxation from interaction between the first and second magnetic nanoparticles can be detected to determine hybridization of both the first and the second targeting probes to the first and the second target. In one preferred embodiment, the first and second polypeptide probes bind to the same target polypeptide. In another preferred embodiment, the first and second polypeptide probes bind to a first and second target polypeptide respectively, such that when the two target polypeptides interact, the first and the second nanoparticle probe compositions are brought in close proximity and generate a measurable effect on water relaxation. The present invention provides that in a preferred embodiment, the polypeptide probe comprises an antibody or antibody fragment and may be attached to the biocompatible coating of the magnetic nanoparticle probe to target a pair of proteins, as illustrated in FIG. 2B. In other embodiments, effective targeting of protein complexes in living cells can be achieved by using other high affinity ligands conjugated to the surface coating of magnetic nanoparticles such as FlAsh or ReASH for tetra cysteine (Cys) tags or Ni for Poly Histidine (His) tags genetically engineered on target proteins. The magnetic contrast can be generated based on targeting of two or more magnetic nanoparticles to the protein complexes. This targeting of magnetic nanoparticles to proteins can be achieved by using antibodies, antibody fragments, peptides, or other high affinity ligands (e.g. Nickel for Poly Histidine tags, GST for Glutathione, etc) attached to the surface of the magnetic nanoparticle biocompatible coating. This magnetic imaging ability can also be combined with fluorescence based measurements using traditional FRET pairs or Lanthanide based FRET measurements.

In a preferred embodiment antibody or antibody fragment may provide advantages as compared to other high affinity ligands for in vivo detection of protein interaction or protein complexes especially in human subjects, since the use of other high affinity ligands requires modification of the proteins, which may only be possible for solution, cellular or animal studies. In certain embodiments other probe molecules such as peptides and aptamers may be incorporated on the surface of the magnetic nanoparticle for protein interaction studies.

The present invention is based on magnetic nanoparticle induced changes in water relaxation. In the presence of a paramagnetic substance, the water relaxation properties, namely $T_1$, $T_2$ and $T_2^*$ ($1/T_2^*=1/T_2+1/T_2'$, with $T_2'$ being a time constant arising from magnetic field inhomogeneity) of proton nuclear spins are shortened to some extent. In a preferred embodiment, paramagnetic or superparamagnetic nanoparticle probes are used to detect specific nucleic acids in tissues and cells, since superparamagnetic iron oxides (SPIO) or superparamagnetic nanoparticles affect the relaxation times in a more significant way.

In certain preferred embodiments, the uniformity of the size of the magnetic nanoparticles is required. There is a strong dependence of water relaxivity on nanoparticle size, with smaller particles having lower relaxivity and a lower ratio of $R_2/R_1$ ($R_1=1/T_1$, $R_2=1/T_2$). The relaxivity also depends on the strength of applied magnetic field. For nanoparticles of ~5 nm in size and the field strength of 3 Tesla, an $R_2$ value of $40(s\,mM(Fe))^{-1}$ is expected with monodispersed nanoparticle probes. When the nanoparticle probes are bound to the mRNA target such that a pair of magnetic nanoparticles is clustered together, an $R_2$ of $100\,(s\,mM(Fe))^{-1}$ is anticipated. This leads to an increase of the $R_2$ value by $60\,(s\,mM(Fe))^{-1}$. Assuming the tissue intrinsic $T_2$ to be 80 ms, a 100 nM Fe concentration introduced by the nanoparticle probes may lead to a $T_2$ of 60 ms and 40 ms respectively with bound and unbound nanoparticle probes. This difference in $T_2$ should be sufficient for clinical imaging applications.

Figure 6:
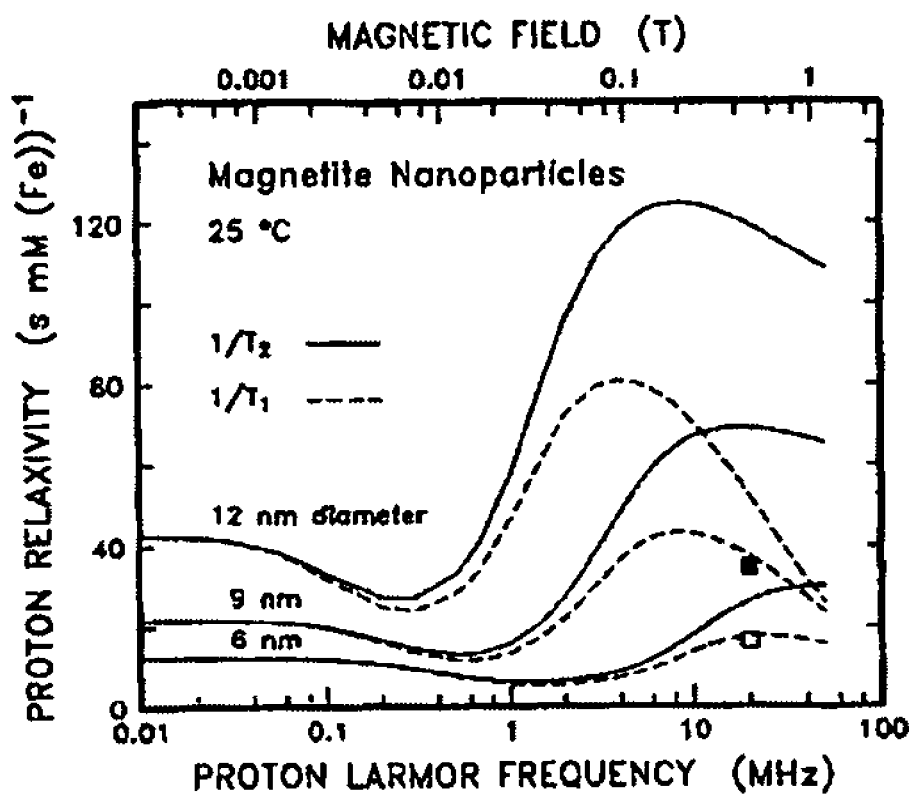
FIG. 6A is a graph showing the predicted proton relaxivity as a function of the magnetic field strength for magnetic nanoparticles with different sizes (adapted from Koenig & Kellar, 1995, Magn. Reson. Med. 34:227-233).
FIG. 6B is a schematic representation showing that when two multifunctional magnetic nanoprobes bind to a single target sequence, the magnetic nanoparticles are in close proximity. Due to direct interactions, the two magnetic nanoparticles should behave as a single, large nanoparticle.
Figure 6:
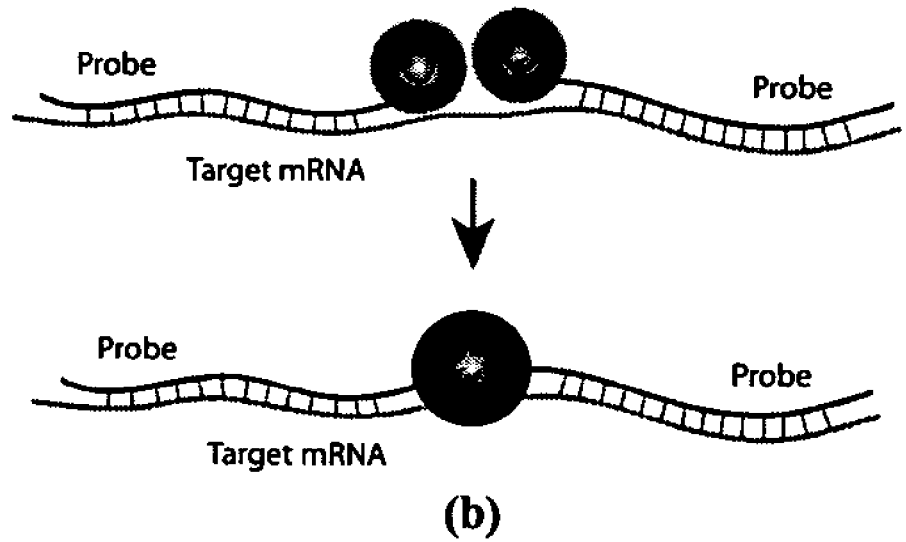

In yet another embodiment, the dependence of $T_2$ on nanoparticle size will be determined. According to the theoretical prediction (Koenig and Kellar, 1995) and experimental measurement (Pouliquen et al, 1992), $R_2$ approximately doubles when the particle is increased from 5-10 nm to 9-15 nm (FIG. 6). When the magnetic nanoparticle probes hybridize with targeted mRNA in vivo, this increase in size will be effectively achieved. For illustrative purposes, assume that the nanoprobe delivery achieves an in vivo concentration of 50 µM of iron (ca. 25 nM of nanoparticle probes), and that at 3 T the value of $T_2$ of the tissue is about 100 ms without contrast agent. In the presence of mRNA targets, hybridization between the magnetic nanoparticle probes and the mRNA targets may lead to a $T_2$ of 48 ms. Even if only half of the nanoprobes are hybridized (corresponding to a target concentration of 12.5 nM), there will be an increase in relaxivity that reduces $T_2$ to 35 ms. With a spin-echo imaging sequence using a TE of 50 ms, a ~30% contrast will be achieved, which is sufficient for visualizing the corresponding cells or tissue.

EXAMPLES

Synthesis and Characterization of Magnetic Nanoparticles

Example 1

Compared with micrometer sized magnetic particles and chelates of paramagnetic ions such as gadolinium diethylenetriaminopentaacetic acid (Gd-DTPA), magnetic nanoparticles are much more efficient as relaxation promoters, and their effect on the relaxivities of water is measurable even at nanomolar concentrations, as demonstrated theoretically and experimentally (Koenig et al., 1995; Bulte et al., 1992; Le Duc, 2001; Josephson et al., 2001; Perez et al., 2002). Specifically, the use of ferromagnetic and superparamagnetic nanoparticles as contrast agents can induce a more than 10 fold increase in proton relaxivities (Coroiu et al., 1999). Based on the enzyme-cleavable contrast agents reported by Meade and coworkers (Louie et al., 2000; Huber et al., 1998), magnetic relaxation by gadolinium atoms is a short-range effect. The presence of a carbohydrate cap (less than 1 nm thick) prevents water molecules from contacting the contrast agent Gd (HP-DO3A). In contrast, superparamagnetic nanoparticles (2-3 nm core size) are often coated by a thick dextran layer (10-20 nm) (Josephson et al., 2001). Despite this coating, the encapsulated nanoparticles are highly efficient contrast agents, yielding considerably stronger effects than gadolinium compounds. Although it is possible that water molecules are able to penetrate the dextran layer, iron oxide nanoparticles are thought to function over a distance range of approximately 2-20 nm.

To facilitate probe/target hybridization and signal transduction, the size of the magnetic nanoparticle with coating should be minimized. Means of obtaining highly monodispersed particles are known in the art. For example, the particles can be synthesized by (i) chemical reduction of $FeCl_2$ and $FeCl_3$ compounds according to published procedures (Shen et al., 1993). Alternatively, the magnetic nanoparticles can be synthesized by (ii) precipitation within the confines of a polymer matrix following an ion-exchange procedure (Mallouk et al., 1996, Chem. Mater. 8:2121-2127), or by (iii) precipitation within micelles (Feltin and Pileni, 1997; Seip and O'Connor, 1999). Of these three methods, precipitation within micelles is the method of choice because it yields magnetic nanoparticles in the desired size range with a narrow size distribution.

In the reverse micelle method, the precipitation of magnetic nanoparticles is confined to aqueous droplets suspended in an immiscible phase, e.g. hydrocarbons. Since the precipitation reaction is entirely confined to nanometer sized water droplets, the size and shape of the nanoparticle depends on the characteristics of the oil-water mixture. The droplets are formed by emulsifying water into a continuous oil phase through the use of surfactants to lower surface energy between the otherwise immiscible phases. The surfactant monomers self-assemble into micelles at a critical concentration. Both oxide nanoparticles with magnetization in the range 5-12 emu/g and metallic nanoparticles capped with a protective coating and with magnetization in the range of 500-800 emu/g can be synthesized. The iron oxide core size and its distribution can be determined by high-resolution transmission electron microscopy (TEM), while the bioconjugated particles can be characterized by using dynamic light scattering, which measures the hydrodynamic radius of nanometer-sized particles in solution.

Figure 3:
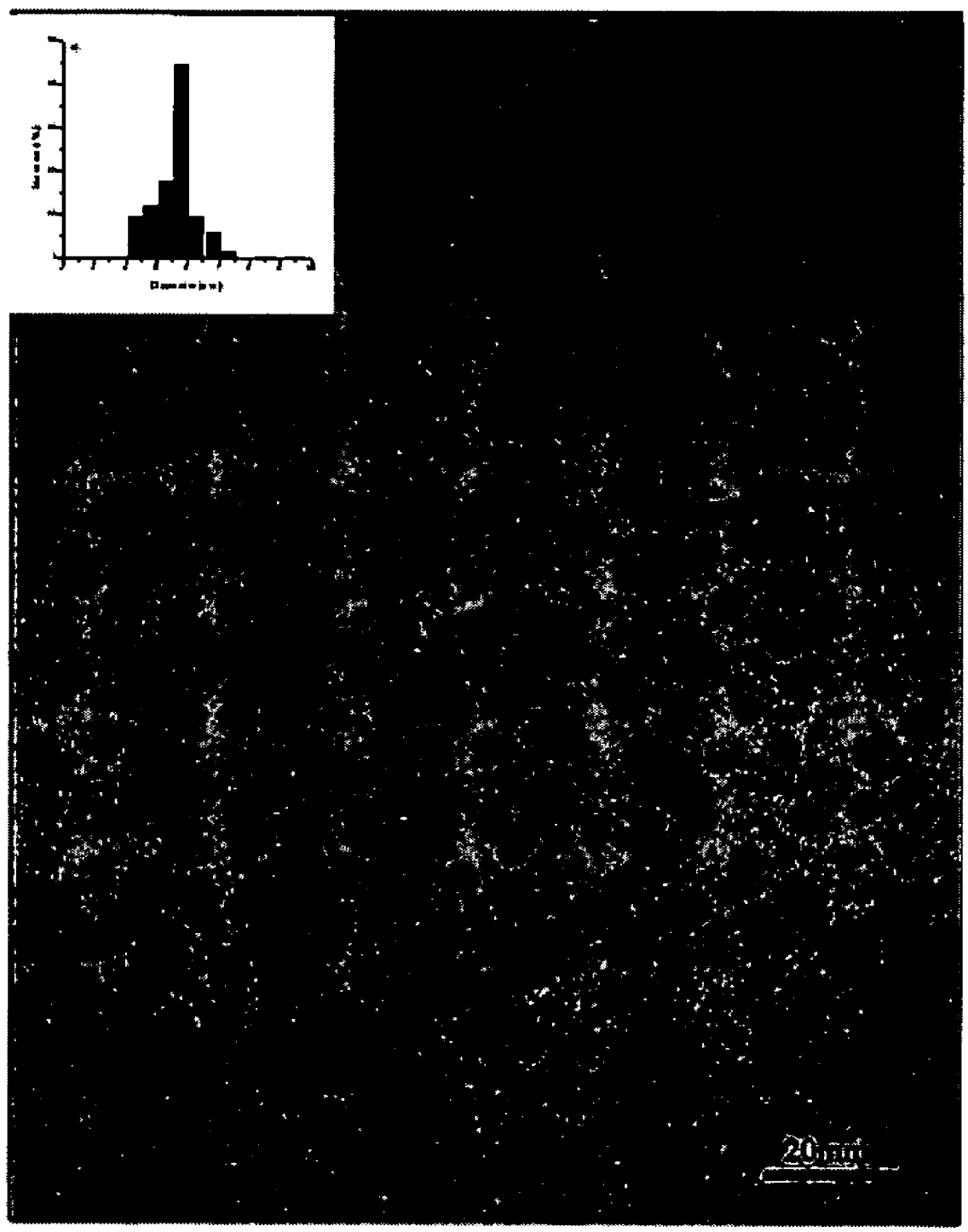
FIG. 3 is transmission electron microscopy image of iron oxide ($Fe_3O_4$) particles with an average size of 6.6 nm and size variation of 11%. The image is courtesy of Dr. Charles O'Connor at the University of New Orleans.

In the studies to be described, magnetic iron oxide nanoparticles (MIONs) with chemical composition $Fe_3O_4$ synthesized using the reverse micelle technique were provided by Dr. Charles O'Connor at the University of New Orleans. These MIONs had an average size of 6.6 nm with a size distribution of 11% as determined by transmission electron microscopy, as shown in FIG. 3 (personal communication, Dr. Charles O'Connor). Due to the synthesis approach, these particles have a residual capping of surfactant molecules such as cetyltrimethylammonium bromide (CTAB), which render these particles soluble only in organic solvents and also prevent aggregation of nanoparticles. Particles used in this study were dispersed in toluene and were insoluble in water prior to modification.

Example 2

Encapsulation of the Magnetic Nanoparticles

A critical component for the success of this invention is to make monocrystalline iron oxide nanoparticles (MIONs) water-soluble and create a stable suspension of MIONs that are biocompatible and surface-functionalized. A standard approach in the field is to use the polysaccharide dextran. A distinct disadvantage to this approach is the large thickness of the coating (approximately 15 nm). In order to minimize steric hindrance in hybridization between two probes, it is crucial to minimize the size of the coating. Therefore, efforts in the present invention were focused on developing alternative coatings. Two such post-synthesis coating processes will be described in detail here.

The first coating uses the monolayer ligand 16-mercaptohexadecanoic acid (Liu and Xu 1995). The MIONs were reacted with the organic surfactant 16-mercaptohexadecanoic acid (MHA). MHA has a carboxylic head group at one end of the molecule that reacts with the surface of the nanoparticle. The other end of MHA terminates with a thiol head group, which provides a reactive functionality to which modified oligonucleotides can be attached. Reaction of MHA with MIONs resulted in a self-assembled monolayer film with exposed, reactive sulfhydryls on the surface of the particle. Since the coating is only a single layer of MHA molecules, this should increase the diameter of the particles by approximately 1.6 nm, since MHA is a chain of 15 carbon atoms. A colorimetric assay based on 5,5-dithiobis(2-nitrobenzoic) acid was used to confirm the presence of exposed sulfhydryl groups (Sedlak and Lindsay, 1968, Anal. Biochem. 25:192-205), which facilitates the conjugation of modified oligonucleotides to MIONs.

Figure 4:
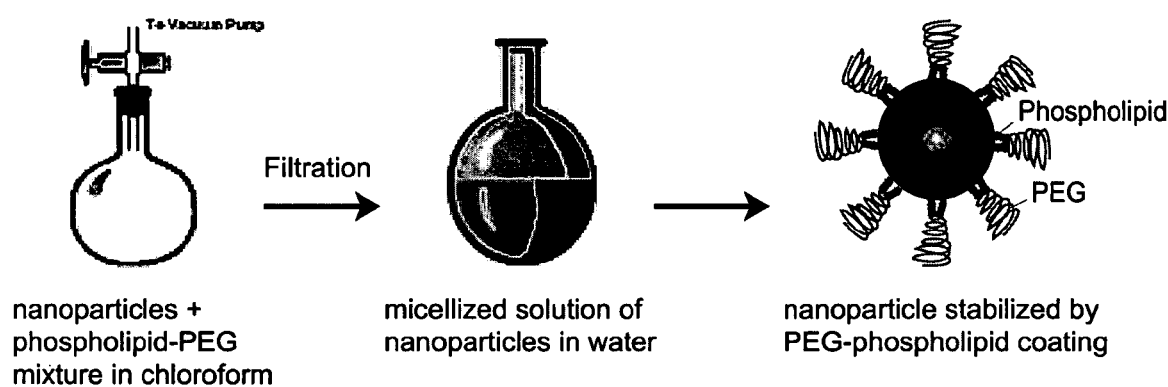
FIG. 4 is a schematic representation of the micellization procedure.

The second coating to be described in detail here exploits the amphiphilic nature of a phospholipid-polyethylene glycol (PEG) molecule (FIG. 4). Mixtures of 1,2-Distearoyl-sn-Glycero-3-Phosphoethanolamine Polyethylene Glycol 2000 (DSPE-PEG 2000) and 1,2-Distearoyl-sn-Glycero-3-Phosphoethanolamine-N-[Amino(Polyethylene Glycol) 2000] (DSPE-PEG 2000 Amine) were dissolved in chloroform (1:8 ratio of DSPE-PEG 2000:DSPE-PEG 2000 Amine) to a total concentration of 1.4 mM, and iron oxide was added to the solution at a concentration of 0.33 mg/ml. This surfactant/ iron oxide solution was then dried under argon gas and left in a vacuum dessicator for 48 hours to remove all traces of organic solvents. The dried film was then easily resuspended in deionized water with agitation. The solution obtained was filtered using 0.2 µm syringe filters to remove aggregates. The resulting filtered solution (referred to as micelle-MIONs) was free from cloudiness and is stable for a period of weeks when kept at 4° C. to prevent bacterial growth. This coating provides biocompatibility and enhances solubility of the MIONs. It also has the added advantage of flexible functionality, since a number of modified PEGs other than PEG-amine are readily available (e.g. PEG-maleimide).

Figure 5:
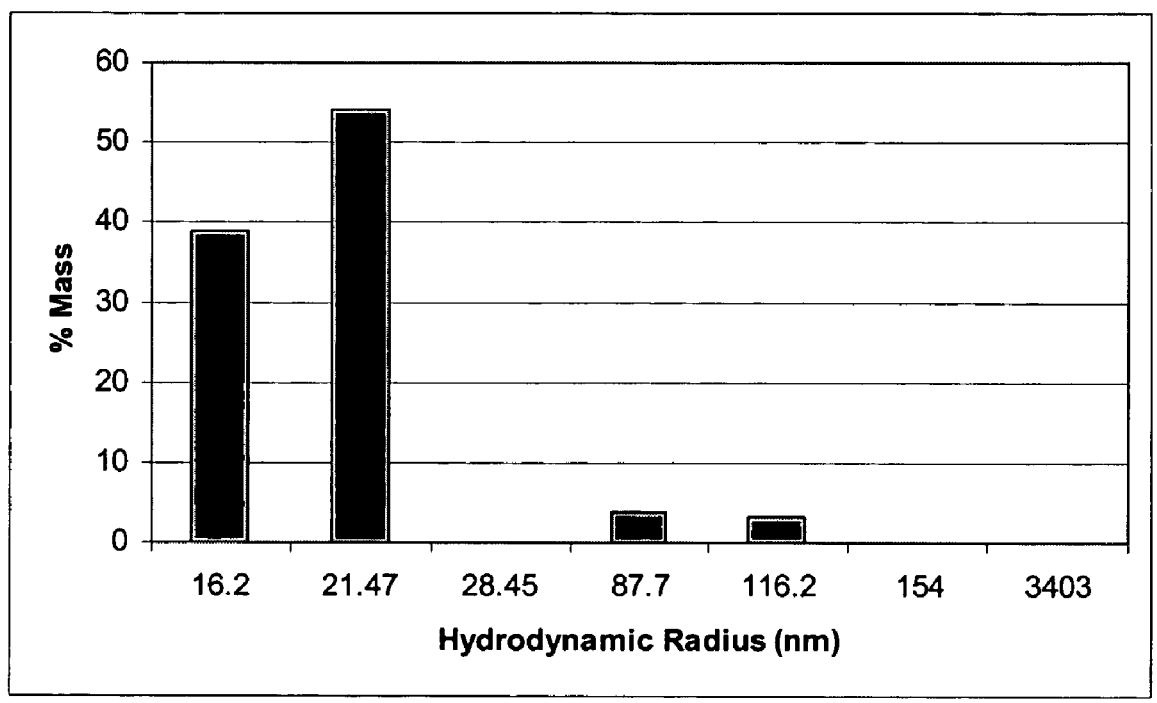
FIG. 5 is a histogram showing the results of dynamic light scattering (DLS), used to determine the size of the micelle-encapsulated magnetic iron oxide nanoparticle (MION) probes.

To determine the size of the micelle-coated MIONs, dynamic light scattering (DLS) using a DynaPro-LSR instrument from Protein Solutions was employed. By fitting the data to a polydispersed model (Braginskaya et al. 1983) using the Dynamics software (version 5.26) provided with the instrument, the average hydrodynamic radius of the micelle-MIONs is 19.3 nm±3 nm, which accounts for 93% of the mass of the sample (FIG. 5).

Example 3

Bioconjugation of Magnetic Nanoparticles to Create Multifunctional Probes for Imaging and Delivery After encapsulation, the particles can be conjugated to peptides, proteins, fluorescent dye molecules, and hairpin oligonucleotide (ODN). Such conjugation is achieved by utilizing the functional group on the surface of the MIONs (in the specific cases described here, either reactive sulfhydryls or amines). These functional groups on the particle surface can be covalently conjugated to any of the above-described moieties by using standard cross-linking chemistry. Below will be described two specific examples of bioconjugation between MIONs and a) delivery peptide plus fluorescent dye and b) oligonucleotides. These examples use micelle-MIONs and MHA-MIONs, respectively; however, the coatings are versatile and either application is possible with both types of particles, with the micelle-MIONs being the preferred embodiment due to their superior solubility.

Figure 10:
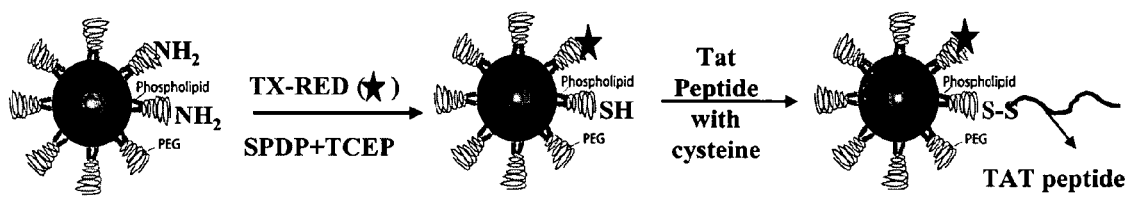
FIG. 10 is a schematic representation of the procedure for the simultaneous fluorescent labeling of and bioconjugation of the magnetic nanoparticles.

For optical imaging and efficient delivery of magnetic nanoparticles, the functionalized lipid-PEG molecules (DSPE-PEG-amine) in the micelle structure were targeted for bioconjugation. Simultaneous attachment of fluorescent dye molecules and a delivery peptide on micelle-MIONs through a reactive amine group was achieved using the strategy shown in FIG. 10. Texas Red STP ester (1 µm) and the heterobifunctional cross-linking reagent, N-succinimidyl 3-(2-pyridyldithio)propionate (SPDP) (10 µm) were used to react with amine groups on the micelle-MIONs. This mixture was allowed to react for 2 hours. The reductant tris(2-carboxyethyl) phosphine hydrochloride (TCEP) was added at 20 mM to reduce the thiol group on SPDP for 1 hour. A Microcon YM10 filter unit was used to remove unreacted TxRed and TCEP. Tat peptide-6-Amino hexonic acid-Cys (for delivery) was reacted overnight with the mMIONs via the SPDP cross linker at a concentration of 1 µM. Unreacted peptide was removed by dialysis into 2 L of PBS buffer using a Slide-A-Lyzer Dialysis Cassette (MWCO 10000) for 4 hours.

The mMIONs with both TxRed and TAT peptide attached were successfully delivered into human dermal fibroblast (HDF) cells and kidney-derived MDBK cells (data not shown). HDF cells were plated on 8-well Nalgene Nunc cell culture plate and allowed to grow for 48 hours. A 1:4 dilution of the original mMIONs-Tx Red-peptide complex in FBM2 media formulation provided by Cambrex (New Jersey) was added to cells and incubated for an hour. Cells were washed in PBS buffer two times and imaged using a Zeiss confocal microscope ((data not shown)). MDBK cells were treated similarly.

Figure 11:
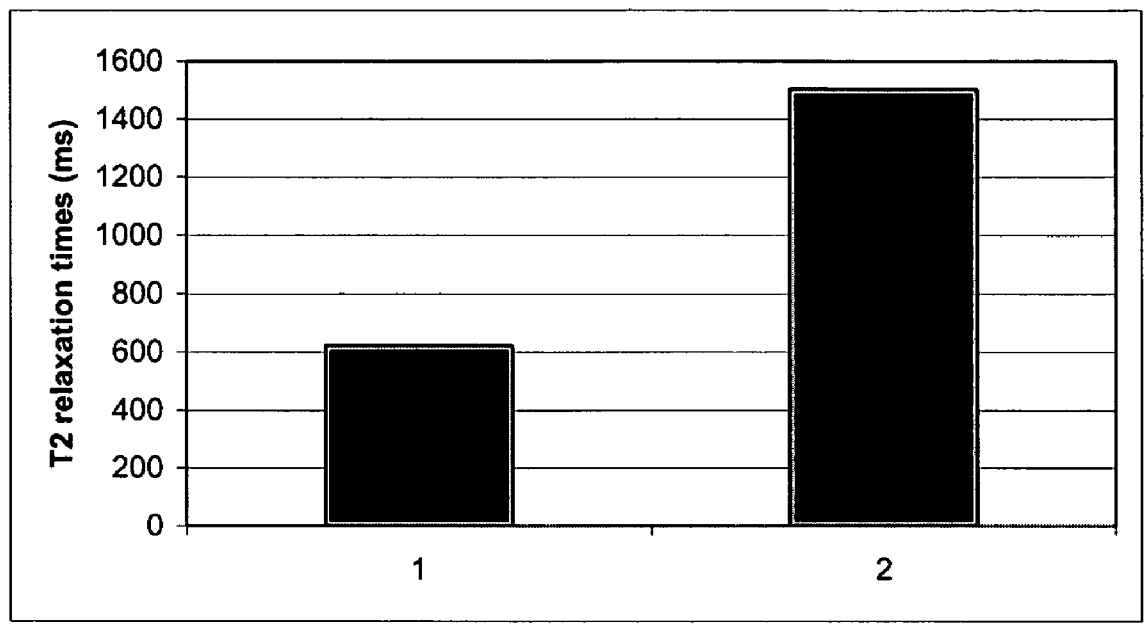
FIG. 11 shows results of magnetic resonance imaging of MDBK cells.
Figure 11:
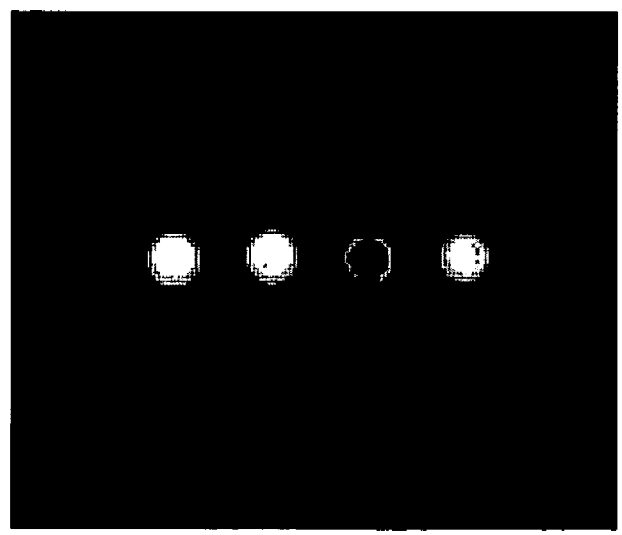

To further validate the delivery of the micelle-MIONs into live MDBK cells, $T_2$ relaxation times were measured and MRI contrast images were obtained. For $T_2$ measurements, a Bruker Minispec Analyzer MQ20 was used. Cells were grown in a T25 culture plate (approximately $10^6$ cells) and then incubated with a 1:4 dilution of mMIONs and media (as above). After 1 hour of incubation, cells were washed two times with PBS buffer and trypsinized to remove the cells from the plate. Cells were resuspended in a final volume of 1.5 ml of media. 500 ul of cell suspension was placed in a 10 mm sample tube for $T_2$ measurements. $T_2$ values were determined using the cpmb sequence. $T_2$ relaxation time determined for cells with mMIONs was 623±2 ins; $T_2$ relaxation time for cells without mMIONS was 1503±20 ms (See FIG. 11(a)). Controls for this experiment were MDBK cells without mMION incubation. This cell sample was then imaged on a 3T Siemens MRI system, and good contrast was obtained for the cells that contained micelle-MIONs (FIG. 11(b)).

Figure 7:
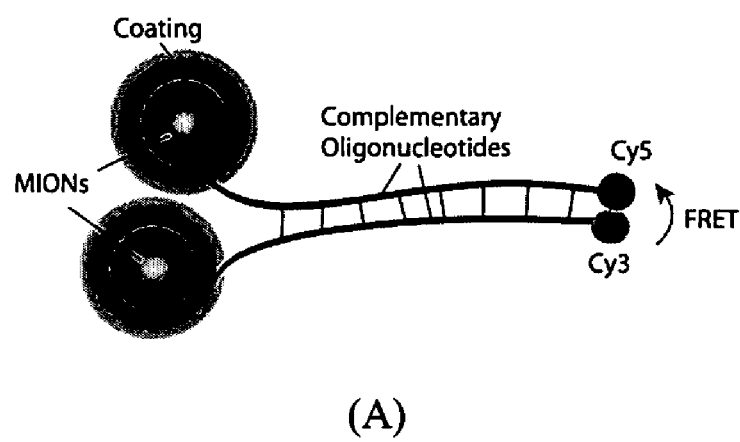
FIG. 7A is a schematic representation of the Fluorescence Resonance Energy Transfer (FRET) assay used to determine the effect of clustering of magnetic nanoparticles. In this embodiment, two MION probes comprise complementary oligonucleotides. The MION probes further comprise a FRET dye (Cy5 for one of the oligonucleotides, and Cy3 for the complementary oligonucleotide). The energy transfer from the donor (Cy3-MION) to the acceptor (Cy5-MION) is detected upon hybridization of the two oligonucleotides.
FIG. 7B shows a strategy to combine optical and MRI imaging of molecular markers in vivo. Donor and acceptor fluorescent dyes conjugated to a pair of magnetic nanoprobes results in a FRET signal when both are bound to the same target mRNA.
Figure 7:
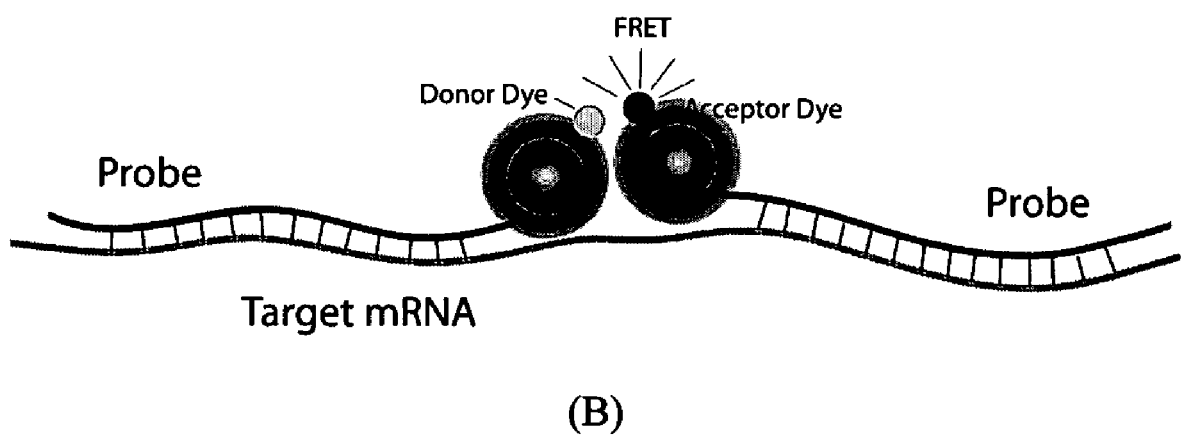

The second bioconjugation scheme to be described employs MIONs coated with MHA and linked to oligonucleotides. Initial studies with MIONs were designed to detect hybridization between two single-stranded oligonucleotides (30-mers) (FIG. 7). For these solution studies, MHA-coated MIONs were attached to complementary oligonucleotides via reaction with their surface sulfhydryl groups. Again, the heterobifunctional cross-linker SPDP was used for the bioconjugation due to its amine and sulfhydryl reactivity. Two complementary oligonucleotides were designed with reactive primary amine groups on their 3' and 5' end, respectively. Their specific sequences are: Probe 1: /Cy3/-5'-GAGTCCT-TCCACGATACTACGATCCACATT-3' (SEQ ID NO:27), Probe 2: /Cy5/-5'-AATGTGGATCGTAGTATCGTCGAAG-GACTC-3' (SEQ ID NO:28).

These oligonucleotides were first coupled to SPDP and then reacted with MHA-coated MIONs that were reduced with TCEP to eliminate any disulfide bonds that might be on the surface. The quantity of oligonucleotides to react was determined by approximating the molar concentration of particles and then reacting oligonucleotides and MIONs in a 1:1 or 2:1 ratio to ensure that there was on the order of one oligonucleotide per nanoparticle. This conjugation was successfully completed as shown by the ability to separate free oligonucleotides from particles both by filtration and magnetically. The resulting solution contained fluorescent particles that behave similarly to unlabeled MIONs, indicating the successful attachment of oligonucleotides with fluorophores. These MIONs conjugated to oligonucleotides were then used in the study described in the following section.

Example 4

Magnetic and Optical Effects of the Close Proximity of Two Multifunctional Magnetic Nanoparticle Probes To detect the hybridization of oligonucleotides attached to MHA-MIONs, a FRET (Fluorescence Resonance Energy Transfer) based assay was developed (FIG. 7). The approach of FRET is based on energy transfer between the donor and the acceptor fluorophores. This process of energy transfer is only efficient if two fluorophores are in close proximity to each other (approximately 5 nm or less). This technique has been used to detect hybridization of oligonucleotides in conventional biochemical studies. For the development of this assay, complimentary oligonucleotides modified at the 3' end and 5' end with a FRET dye pair, Cy3 and Cy5, were attached to MHA-MIONs to produce Cy3-MION and Cy5-MION, respectively. The energy transfer from the donor (Cy3-MION) to the acceptor (Cy5-MION) is detected upon hybridization.

Figure 8:
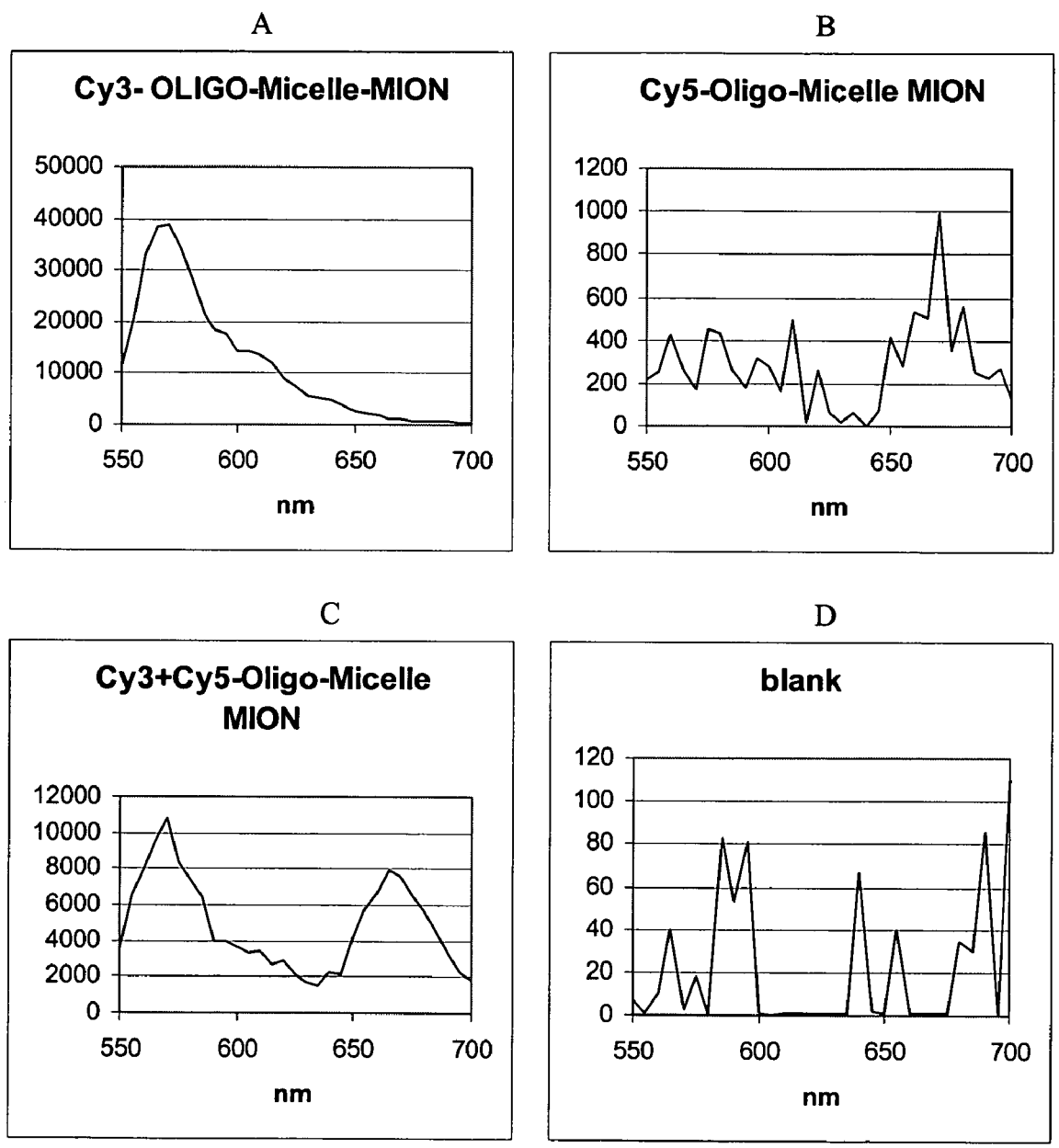
FIG. 8A-8D show graphs of the results of optical detection using FRET for the A) Cy3-oligonucleotide-micelle-MION probe+Cy5-oligonucleotide-micelle-MION probe combination, B) Cy3-oligonucleotide-micelle-MION probe alone, C) Cy5-oligonucleotide-micelle-MION probe alone, and D) a blank sample. Samples were excited at 500 nm to eliminate any significant direct excitation of the Cy5 dye.

For the hybridization assay, Cy3-MION and Cy5-MION were mixed together (Cy3-MION+Cy5-MION). For the FRET studies, we maintained a constant oligonucleotide concentration for all samples (Cy3-MION, Cy5-MION, and Cy3-MION+Cy5-MION). All samples were excited at 500 nm to eliminate any significant direct excitation of the Cy5 dye. The emission wavelength was scanned from 570 nm-700 nm. The emission peak for the Cy3 dye is 570 nm, and for the Cy5, it is 675 nm. A representative FRET dataset is shown in FIG. 8. In the Cy3-MION+Cy5-MION sample, the Cy3 signal intensity has decreased and the Cy5 signal has increased relative to the individual samples (Cy3-MION, Cy5-MION). The signal intensity detected in this assay was much lower than the signal intensity detected in standard hybridization studies using oligonucleotide pairs, due to steric hindrance of the MION coated particles and also the stringent requirement to have 1-2 oligonucleotides per particle. The FRET study results indicated that the complementary oligonucleotides of the Cy3-MION+Cy5-MION sample were hybridized.

Magnetic Resonance Imaging (MRI) Contrast agents such as the one described in this invention are often used in MRI to enhance lesion detection. For clinical diagnostic imaging, paramagnetic substances such as chelates of gadolinium are frequently used as contrast agents. In the presence of such a paramagnetic substance, the relaxation properties, namely $T_1$, $T_2$ and $T_2^*$ ($1/T_2^* = 1/T_2 + 1/T_2'$, with $T_2'$ being a time constant arising from magnetic field inhomogeneity) of proton nuclear spins are shortened to some extent. Theoretically, proton relaxivities $R_1 = 1/T_1$ and $R_2 = 1/T_2$ change with the size of magnetic nanoparticles (Koenig et al., 1995) as illustrated by FIG. 6(a) in which $R_1$ and $R_2$ profiles were predicted for magnetic nanoparticles of 6, 9 and 12 nm in diameter at 25° C. It is seen from FIG. 6(a) that when the size of the nanoparticles increases from 6 to 12 nm, the value of $R_2$ is doubled. This is consistent with the experimental evidence showing that stable clustering of magnetic nanoparticles can generate a measurable change in the relaxation effects. For example, when several caged superparamagnetic particles (3 nm) were clustered due to binding between attached oligonucleotide probes and complementary targets in solution, there was a two-fold increase in the $R_2$ of water (Josephson et al., 2001). Similarly, self-hybridization of two complementary oligonucleotides with conjugated magnetic nanoparticles reduced the relaxation time $T_2$ by a factor of 2 (from 61 ms to 32 ms) (Perez et al., 2002.).

When two oligonucleotide probes are designed such that they hybridize to the same target mRNA in a head-to-head fashion, as illustrated in FIG. 6(b), or hybridize to each other, as illustrated in FIG. 7, the two conjugated magnetic nanoparticles may act together, generating an 'effective' particle that is about twice as large as the individual nanoparticles, and leading to dramatically enhanced effect on the relaxivities $R_2$ and/or $R_1$. Such an effect is readily measurable with MRI.

To evaluate the difference between the MRI signal generated by the hybridized complex as compared to the individual oligonucleotide samples T2 relaxation time was measured for the same samples used for the optical detection using FRET. In this assay, the total MION particle concentration in the Cy3-MION Cy5-MION sample was the average of the MION concentration in the individual samples (Cy3-MION, Cy5-MION). Even though the samples initially had the same concentration of MION particles for conjugation of the oligonucleotides, there are small variations in concentration of the two samples (Cy3-MION, Cy5-MION). The MRI results are shown in Table 1. The results clearly indicate a shift in the T2 relaxation time (ins) of the Cy3-MION Cy5-MION as compared to the Cy3-MION and Cy5-MION samples.

TABLE 1

| Sample | Trial 1 T2 (ms) | Trial 2 T2 (ms) |
| --- | --- | --- |
| Cy3-MION | 920.4 | 546.1 |
| Cy5-MION | 726.4 | 469.2 |
| CY3-MION + CY5-MION (predicted) | 823.4 | 507.65 |
| CY3-MION + CY5-MION (obtained) | 713.8 | 426.9 |

It is predicted that the $T_2$ value of the Cy3-MION+Cy5-MION sample will be lower than that of the individual samples (Cy3-MION, Cy5-MION) because hybridized sample of oligonucleotides will bring the MIONs in close proximity, effectively increasing their local magnetic field strength and thus affecting their relaxation behavior.

Figure 9:
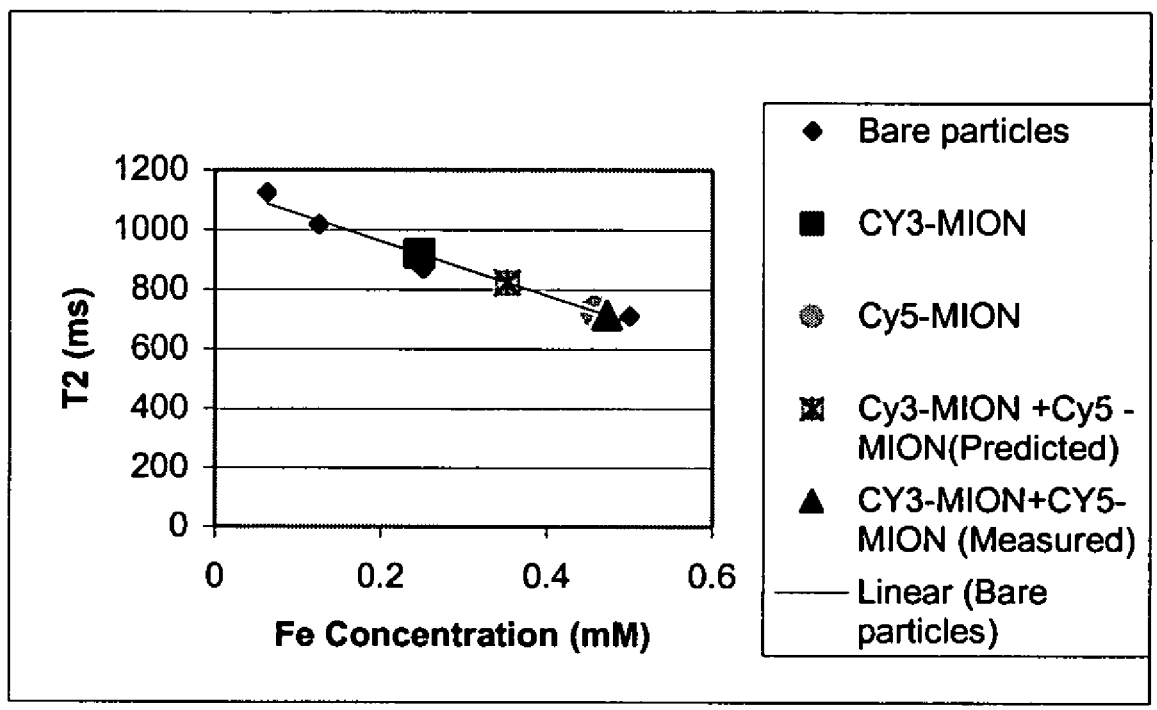
FIG. 9 is a graph showing the $T_2$ relaxivity of the samples as a function of the MION (Fe) concentration. The diamonds represent bare particles, and the line connecting the diamonds represents a calibration curve for the particles. The square and the circle represent the Cy3-MION probe and the Cy5-MION probe, respectively. The square with the star represents the predicted value for the combination of the Cy3-MION probe and the Cy5-MION probe. The triangle represents the actual value, which is decreased, indicating an effect of interaction of the two MION probes.

To develop more quantitative understanding of the response of $T_2$ relaxivities as a function of MION concentration, the $T_2$ relaxivities of a serial dilution of the MION sample were measured, and a calibration curve for $T_2$ relaxation times vs. MION (Fe) concentration was developed. The calibration plot is shown in FIG. 9. Based on this standard curve, the response in $T_2$ relaxation times was estimated for the CY3-MION+CY5-MION sample, as compared to the individual samples (Cy3-MION, Cy5-MION). The results are shown in FIG. 9. The results of the comparison show a significant shift in the effective concentration of the MION particles for the Cy3-MION+Cy5-MION, indicating an effect of the interaction of magnetic particles. The hybridized MION's show an effective concentration 34% higher than that predicted value based on the single MION particle concentration. These results indicate that is possible to distinguish between scattered and clustered multifunctional magnetic nanoparticle probes of the present invention, using both a FRET-based assay and magnetic resonance imaging. Optimization of the design will focus on oligonucleotide structure. Specifically, for the design proposed in FIG. 6b, the size of the gap between the probe sections on the target will be varied to determine the optimal length necessary for maximum contrast without compromising hybridization of the probes to the target mRNA.

Example 5

Use of Magnetic Nanoparticle Probes to Detect Viral Infection or Traumatic Injury in Rats The first model involves a viral infection (influenza virus A) in rats. Virus is injected into one of animal's hind leg and allowed to develop for 24 hours before imaging. The nanoprobes, designed to target the eotaxin mRNA, are then be injected. The imaging studies will compare the two hind legs and also assess the heterogeneity of the infected leg. Contrast will be quantitatively assessed by comparing image intensity of the infected leg with the control leg.

The second model is a brain injury model of rats induced by inertial acceleration. It has been shown that the mRNA expression of cytochrome c oxidase II (COII), a mitochondrial encoded subunit of complex IV, is upregulated following traumatic brain injury (TBI). The severity of the injury will be made very low so that no edema will be present and little contrast is seen on conventional MRI. The animal will be imaged before the injury, after the injury but without the nanoprobes, and after the injury with nanoprobes. Contrast to noise ratios between the injured area and the surrounding tissue will be calculated.

Previous in vivo studies in the liver demonstrated robust contrast at a spatial resolution of 1 mm. That study was performed at 0.47 T and using a human head coil. For the proposed studies, a specialized coil will be used that is much smaller than the head coil used in the liver study. The studies will be performed at 3 T. With the increase in field strength and coil sensitivity, which will increase the signal-to-noise ratio and the relaxation effect of the magnetic nanoparticles, we expect a substantial increase in detection sensitivity, allowing us to achieve a resolution of 0.1 mm in mice. This resolution should be sufficient for studying infected areas with sufficient spatial resolution.

Example 6

Use of Multifunctional Magnetic Nanoparticle Probes to Detect Cancer

It is well established that cancer cells develop due to genetic alterations in oncogenes and tumor suppressor genes and abnormalities in gene expression that provide growth advantage and metastatic potential to the cells. A critical step in diagnosing and treating cancer in its early stages is to detect cancer cells based on the genetic alterations.

A novel way of achieving early detection of cancer is to identify cancer cells through detection of mRNA transcripts that exist in cancer cells but not in normal cells. The multifunctional magnetic nanoparticle probes of the present invention could be utilized for the early detection of cancer cells, using optical imaging or magnetic resonance imaging.

EXAMPLE 7

Specific mRNA Detection in Living Cells Using Peptide-linked Nucleic Acid Probes To demonstrate the rapid and sensitive detection of mRNA in living cells, we developed peptide-linked nucleic acid probes that possess self-delivery, targeting and reporting functions. We conjugated the TAT peptide to nucleic acid probes using three different linkages and demonstrated that, at relatively low ($\geq 200$ nM) concentrations, these nucleic acid probe constructs were internalized into living cells within 30 minutes with nearly 100% efficiency. Further, pep-tide-based delivery did not interfere with either specific targeting by or hybridization-induced fluorescence of the probes.

We could therefore detect human GAPDH and Survivin mRNAs in living cells fluorescently, revealing intriguing intracellular localization patterns of mRNA.

We designed and synthesized peptide-linked nucleic acid probes targeting the human GAPDH (glyceraldehyde 3-phosphate dehydrogenase) and survivin mRNAs, as well as nucleic acid probes with a 'random' probe sequence. The specific design of these nucleic acid probes, and the sequence of the 11 amino-acid TAT-1 peptide used in the study are shown in Table 2. The GAPDH beacon is comprised of a 19-base probe domain targeting the Exon 6 region of GAPDH gene flanked by complementary 5-base sequences that hybridize to form the stem. The survivin beacon has a 16-base target sequence with a similar design of the stem. The 'random' beacon was designed as a negative control, with a 17-base probe sequence that does not have any match in the entire human genome.

Figure 12:
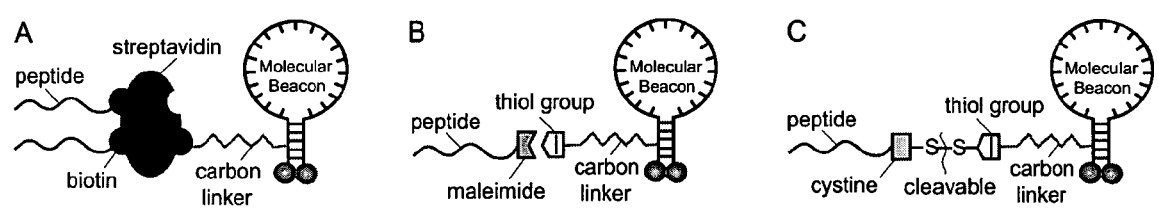
FIG. 12 is a schematic illustration of three different conjugation schemes for linking the delivery peptide to nucleic acid probes. (A) The streptavidin-biotin linkage in which a nucleic acid probe is modified by introducing a biotin-dT to the quencher arm of the stem through a carbon-12 spacer. The biotin-modified peptides are linked to the modified nucleic acid probe through a streptavidin molecule, which has four biotin-binding sites. (B) The thiol-maleimide linkage in which the quencher-arm of the nucleic acid probe stem is modified by adding a thiol group which can react with a maleimide group placed to the C terminus of the peptide to form a direct, stable linkage. (C) The cleavable disulfide bridge in which the peptide is modified by adding a cysteine residue at the C terminus which forms a disulfide bridge with the thiol-modified nucleic acid probe. This disulfide bridge design allows the peptide to be cleaved from the nucleic acid probe by the reducing environment of the cytoplasm.

Three conjugation strategies were developed in attaching the delivery peptide to nucleic acid probes, as illustrated in FIG. 12 In the first approach (FIG. 12A), peptides were linked to a nucleic acid probe through a streptavidin-biotin bridge by introducing a modified oligonucleotide, biotin-dT, to the quencher arm of the stem through a carbon- 12 spacer. The peptide-linked nucleic acid probe consisted the biotin-modified nucleic acid probe, a streptavidin molecule, and biotin-modified TAT-1 peptides. Since each streptavidin molecule has four biotin-binding sites, we were able to link biotin-modified nucleic acid probes and delivery peptides on the same streptavidin molecule. The stoichiometry was controlled so that the probability of having more than one nucleic acid probes linked to the same streptavidin is small. In the second design (FIG. 12B), we placed a thiol group to the quencher-arm of the nucleic acid probe stem through a carbon linker; the thiol group then reacted with a maleimide group added to the C terminus of the peptide to form a thiol-maleimide linkage (FIG. 12B). Both the streptavidin-biotin bridge and the thiol-maleimide linkage are stable in the cell cytoplasm. As the third approach, we functionalized the TAT-1 peptide by adding a cysteine residue at the C terminus which forms a disulfide bridge with the thiol-modified nucleic acid probe as shown in FIG. 12C. This cleavable design was based on the rationale that the reducing environment of the cytoplasm will cleave the disulfide bond once the construct enters the cell, thereby separating peptide from probe.

TABLE 3

Design of peptide-linked molecular beacons

| | Peptide | |
|---|---|---|
| TAT | (N terminus)TyrGlyArgLysLysArgArgGlnArgArgArg(C terminus) | (SEQ ID NO:29) |
| | Modified Molecular Beacons | |
| GAPDH | 5'-Cy3-<u>CGACG</u>GAGTCCTTCCACGATACCA<u>CG</u>/thiol-d<u>T</u>/<u>CG</u>-BHQ2-3' | (SEQ ID NO:30) |
| Survivin | 5'-Cy3-<u>CGACG</u>GAGAAAGGGCTGCCA<u>CG</u>/thiol-d<u>T</u>/<u>CG</u>-BHQ2-3' | (SEQ ID NO:31) |
| Random | 5'-Cy3-<u>CGACG</u>CGACAAGCGCACCGATA<u>CG</u>/thiol-d<u>T</u>/<u>CG</u>-BHQ2-3' | (SEQ ID NO:32) |

Primary human dermal fibroblast (HDF) cells (Cambrex, N.J.) and a pancreatic cancer cell line MiaPaca-2 (ATCC, VA) were used for this study. These cells were cultured in an 8-well Nalge Nunc culture plate with a glass coverslip bottom in their respective cell culture media for 24 hours prior to experiments. Delivery assays were performed by incubating cells at 37° C. with the media containing peptide-linked nucleic acid probes. For nucleic acid probes targeting GAPDH, peptide-linked nucleic acid probes with three different concentrations (0.25 µM, 0.5 µM and 1.0 µM) were incubated with HDF cells for 30, 60 and 90 minutes. For nucleic acid probes targeting survivin, 0.5 µM of peptide-linked nucleic acid probes were incubated with HDF and MiaPaca-2 cells for 30 minutes. For all assays, the cells were washed twice with PBS to remove the incubation medium and placed in fresh medium for fluorescence imaging, which was carried out using a confocal microscope (Axiovert LSM-100, Zeiss).

To demonstrate the self-delivery and mRNA targeting functions of peptide-linked nucleic acid probes, we first detected mRNA of a housekeeping gene human GAPDH in normal human dermal fibroblast (HDF) cells. After just 30 minutes of incubation with TAT-peptide conjugated GAPDH-targeting nucleic acid probes, we observed clear and localized fluorescence signal in HDF cells as a result of nucleic acid probe-target mRNA hybridization for all three conjugation schemes, i.e., thiol-maleimide, disulfide bridge and streptavidin-biotin (data not shown). In contrast, peptide-linked random-sequence nucleic acid probes with streptavidin-biotin conjugation gave essentially no signal 30 minutes after delivery (data not shown). Similar results were obtained using random-sequence nucleic acid probes with thiol-maleimide and disulfide linkages for peptide (data not shown). This demonstrates that peptide-linked nucleic acid probes remained highly specific in living cells after internalization. Further, we found that GAPDH mRNAs displayed a very intriguing filament-like localization pattern in HDF cells, with a clear tendency of surrounding the cell nucleus and following the cell morphology (data not shown). Interestingly, nucleic acid probes with the cleavable (thiol-cysteine disulfide bridge) design seemed to give better localization patterns than those with the thiol-maleimide linkage, and the latter seemed to perform better than nucleic acid probes with the streptavidin-biotin linkage. Cleavage of the delivery peptide from the construct may have provided nucleic acid probes a better access to target mRNA molecules, although more studies of this phenomenon are required to validate this assumption. It is likely that a nucleic acid probe with a relatively bulky streptavidin molecule is less able to penetrate into the secondary structure of the GAPDH mRNA, thus reducing its ability to seek out its targets. Almost all the HDF cells exposed to GAPDH peptide-linked nucleic acid probes showed strong fluorescence signal, implying a near 100% delivery efficiency (data not shown).

Similar results were obtained after 60 minutes of incubation (data not shown). About the same level of fluorescence was observed for GAPDH-targeting nucleic acid probes with different linkages for peptide, whereas the random-sequence nucleic acid probes did not give much signal. Even after 90 minutes, there was essentially no increase in the signal level (data not shown), indicating that most of the peptide-linked nucleic acid probes entered the HDF cells within the first 30 minutes. Further, fluorescence signal levels and mRNA localization patterns in HDF cells were similar for experiments at three different nominal nucleic acid probe concentrations (0.25 µM, 0.5µM and 1.0 µM). Due to the peptide conjugation process, it was estimated that, with 0.25 µM nominal nucleic acid probe concentration, the actual concentration of peptide-linked nucleic acid probes used in the assay was about 150-200 nM.

Figure 13:
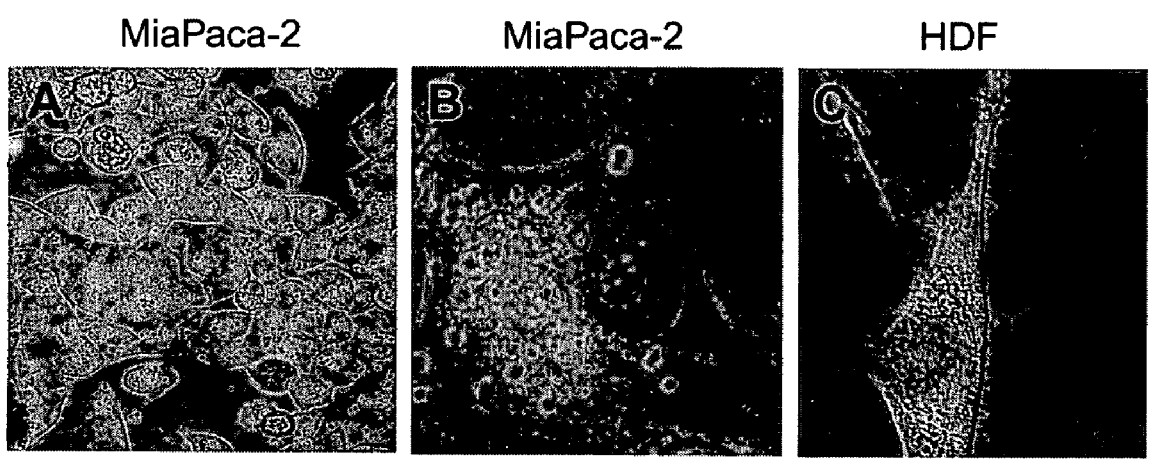
FIG. 13 shows the detection of Survivin mRNA in live HDF and MiaPaca-2 cells. (A) Strong fluorescence signal was observed in MiaPaca-2 cells after 60 min of incubation with peptide-linked nucleic acid probes. Note that essentially all cells shown fluorescence. (B) Survivin mRNA molecules in MiaPaca-2 cells seemed to be concentrated near one side of the cell nucleus HDF cells. (C) Only very low fluorescence signal can be observed in HDF cells, but with a survivin mRNA localization pattern.

To demonstrate the ability of nucleic acid probes to determine gene transcription levels, we observed expression of Survivin mRNA in live HDF and MiaPaca-2 cells. We and others have demonstrated that the Survivin expression level is very low in HDF cells, whereas in MiaPaCa-2 cells the level is relatively high. After 60 minutes of incubation with peptide-linked nucleic acid probes, the fluorescence signal in MiaPaca-2 cells was quite high, as shown in FIG. 13A, but in HDF cells, only very low fluorescence signal can be observed (FIG. 13C). In addition, Survivin mRNAs shown an intriguing localization pattern, i.e., the Survivin mRNA molecules in MiaPaCa-2 cells seemed to be concentrated near one side of the cell nucleus (FIG. 13B). Although with very low expression level, Survivin mRNA localized in HDF in a similar fashion (FIG. 13C). Previous research suggested that the expression level and localization of Survivin may be an important indicator for cancer progression or prognosis.

REFERENCES

Bernacchi, S., and Y. Mely. 2001. *Nucleic Acids Res.* 29:E62-2.
Bonnet, G., S. Tyagi, A. Libchaber, and F. R. Kramer. 1999. *Proc. Natl. Acad. Sci. USA* 96: 6171-6176.
Bonnet, G., Krichevsky, O. and Libchaber, A. 1998. *Proc. Natl. Acad. Sci. USA,* 95, 8602-8606.
Cardullo, R. A., Agrawal, S., Flores, C., Zamecnik, P. C., Wolf, D. E. 1998. *Proc. Natl. Acad. Sci. USA*. 85, 8790-8794.
Chen, W., Martinez, G. and Mulchandani, A. 2000. *Anal. Biochem.,* 280, 166-172.
de Baar, M. P., Timmermans, E. C., Bakker, M., de Rooij, E., van Gemen, B. and Goudsmit, J. 2001. *J. Clin. Microbiol.,* 39, 1895-1902.
Evangelista, R. A., A. Pollak, B. Allore, E. F. Templeton, R. C. Morton, and E. P. Diamandis. 1988. *Clin. Biochem.* 21:173-178.
Fang, X., J. J. Li, and W. Tan. 2000. *Anal. Chem.* 72:3280-3285.
Goddard, N. L., Bonnet, G., Krichevsky, O., Libchaber, A. 2000. *Phys. Rev. Lett.,* 85, 2400-2403.
Kuhn, H., Demidov, V. V., Coull, J. M., Fiandaca, M. J., Gildea, B. D. and Frank-Kamenetskii, M. D. 2002. *J Am Chem Soc.,* 124, 1097-1103.
Li, J. J., R. Geyer, and W. Tan. 2000. *Nucleic Acids Res.* 28:E52.
Liu, J., P. Feldman, and T. D. Chung. 2002. *Anal. Biochem.* 300:40-45.
Liu, Q. and Z. Xu (1995). *Langmuir* 11: 4617.
Lemmetyinen, H., E. Vuorimaa, A. Jutila, V. M. Mukkala, H. Takalo, and J. Kankare. 2000. *Luminescence* 15:341-350.
Lopez, E., C. Chypre, B. Alpha, and G. Mathis. 1993. *Clin. Chem.* 39:196-201.
Marras, S. A., Kramer, F. R. and Tyagi, S. (1999). *Genet. Anal.,* 14, 151-156.8.
Matsuo, T. 1998. *Biochim. Biophys. Acta* 1379:178-184.
Mergny, J. L., A. S. Boutorine, T. Garestier, F. Belloc, M. Rougee, N. V. Bulychev, A. A. Koshkin, J. Bourson, A. V. Lebedev, and B. Valeur. 1994. *Nucleic Acids Res.* 22: 920-928.
Mitchell, P. 2001. *Nat. Biotechnol.* 19:1013-1017.
Molenaar, C., S. A. Marras, J. C. Slats, J. C. Truffert, M. Lemaitre, A. K. Raap, R. W. Dirks, and H. J. Tanke. 2001. *Nucleic Acids Res.* 29:E89-9.
Pouliquen D, Pyrroud H, Calza F, Jallet P, Le Jeune J J. 1992. *Magn Reson Med* 24, 75-84.

Schwartz, J. J. and Zhang, S. 2000. Peptide-mediated cellular delivery. *Curr. Opin. Mol. Ther.* 2: 162-167.

Sei-Iida, Y., H. Koshimoto, S. Kondo, and A. Tsuji. 2000. *Nucleic Acids Res.* 28:E59.

Sixou, S., F. C. Szoka, Jr., G. A. Green, B. Giusti, G. Zon, and D. J. Chin. 1994. *Nucleic Acids Res.* 22:662-668.

Sokol, D. L., X. Zhang, P. Lu, and A. M. Gewirtz. 1998. *Proc. Natl. Acad. Sci. USA* 95:11538-11543.

Sueda, S., J. Yuan, and K. Matsumoto. 2000. *Bioconjug. Chem.* 11:827-831.

Tsourkas, A., Behlke, M. A. & Bao, G. (2002a) *Nucleic Acids Res.* 30: 4208-4215.

Tsourkas, A., Behlke, M. A. and Bao, G. (2002b), *Nucleic Acids Res.* 30: 5168-5174.

Tsourkas, A.; Behlke, M. A.; Rose, S. D. and Bao, G. (2003a). *Nucleic Acids Res.* 31: 1319-1330.

Tsourkas, A., Behlke, M. A., Xu, Y. & Bao, G. (2003b). *Anal. Chem.* 75: 3697-3703.

Tsuji, A., Y. Sato, M. Hirano, T. Suga, H. Koshimoto, T. Taguchi, and S. Ohsuka. 2001. Biophys J. 81:501-515.

Tsuji, A., H. Koshimoto, Y. Sato, M. Hirano, Y. Sei-Iida, S. Kondo, and K. Ishibashi. 2000. Biophys J. 78:3260-3274.

Tyagi, S. and F. R. Kramer. 1996. *Nat. Biotechnol.* 14:303-308.

Vogelstein, B. and Kinzler, K. W. 1999. Digital PCR. *Proc. Natl. Acad. Sci. USA,* 96, 9236-9241.

Yuan, J., K. Matsumoto, and H. Kimura. 1998. *Anal. Chem.* 70:596-601.

Braginskaya, Dobitchin, et al. (1983). *Physica Scripta* 28: 73-79.

Bulte, J. W. M., T. Douglas, et al. (2001). *Nat Biotechnol* 19: 1141-1147.

Burke, N. A. D., H. D. H. Stover, et al. (2002). *Chem. Mater.* 14: 4752-4761.

Butterworth, M. D., L. Illum, et al. (2001). *Colloids and Surfaces A: Physicochemical and Engineering Aspects* 179: 93-102.

Dressman, D., H. Yan, et al. (2003). *Proc Natl Acad Sci USA* 100(14): 8817-8822.

Dubertret, B., P. Skourides, et al. (2002). *Science* 298(5599): 1759-1762.

Dyal, A., K. Loos, et al. (2003). *Journal of the American Chemical Society* 125(1684-1685).

Feltin, N. and M. P. Pileni (1997). *Langmuir* 13: 3927-3933.

Gref, R., P. Couvreur, et al. (2003). *Biomaterials* 24(24): 4529-4537.

Harris, L. A., J. D. Goff, et al. (2003). *Chem Mater* 15: 1367-1377.

Jones, M. and J. Leroux (1999). *Eur J Pharm Biopharm* 48(2): 101-111.

Kim, D. K., M. Mikhaylova, et al. (2003). *Chem Mater* 15: 1617-1627.

Lewin, M., N. Carlesso, et al. (2000). *Nat Biotechnol.* 18(4): 410-414.

Lu, Y., Y. Yin, et al. (2002). *Nano Letters* 2(3): 183-186.

Perez, J. M., T. O'Loughin, et al. (2002). *Journal of the American Chemical Society* 124(12): 2856-2857.

Perkins, W. R., I. Ahmad, et al. (2000). *Int J Pharm* 200(1): 27-39.

Santra, S., R. Tapec, et al. (2001). *Langmuir* 17: 2900-2906.

Seip, C. T. and C. J. O'Connor (1999). *NanoStructured Materials* 12: 183-186.

Torchilin, V. P. (2002). *Adv Drug Deliv Rev.* 54(2): 235-252.

Yee, C., G. Kataby, et al. (1999). *Langmuir* 15: 7111-7115.

Zhao, M., M. F. Kircher, et al. (2002). *Bioconjug Chem* 13(4): 840-844.

Koenig, S. H. and Kellar, K. E. 1995. *Magn Reson Med* 34,227-233.

Bulte, J. W. M., Hoekstra, Y., Kamman, R. L., Magin, R. L., Webb, A. G., Briggs, R. W., Go, K. G., Hulstaert, C. E., Miltenyi, S., The, T. H., and de Leij, D. 1992. *Magn. Reson. Med.* 25, 148-157.

Le Duc, G., Vander, E. L., Colet, J. M., Roch, A., Gillis, P., Le Bas, J. F., Muller, R. N. 2001. *J Magn Reson Imaging.* 13, 619-26.

Josephson, L., Perez, M. and Weissleder, R. 2001. *Angew Chem Int Ed* 40, 3204-3206.

Perez, J. M., O'Loughin, T., Simeone, F. J., Weissleder, R., Josephson, L. 2002. *J Am Chem Soc.* 124, 2856-7.

Coroiu et al, 1999. *J Magn Magn Mater* 201, 449-452.

Louie, A. Y., Huber, M. M., Ahrens, E. T., Rothbacher, U., Moats, R., Jacobs, R. E., Fraser, S. E., Meade, T. J. 2000. *Nat Biotechnol.* 18, 321-325.

Huber, M. M., Staubli, A. B., Kustedjo, K., Gray, M. H., Shih, J., Fraser, S. E., Jacobs, R. E., Meade, T. J. 1998. *Bioconjug Chem.* 9, 242-249.

Throughout this application, various publications are referenced. The disclosures of all of these publications and those references cited within those publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only. Those skilled in the art will recognize, or will be able to ascertain using no more than routine experimentation, many equivalents to the specific embodiments of the invention described herein. Such equivalents are intended to be encompassed by the following claims.

We claim:

1. A nanoparticle probe composition for facilitating molecular imaging or monitoring, comprising:
   a detectable moiety comprising a magnetic nanoparticle having a biocompatible coating thereon;
   a targeting probe attached to the biocompatible coating, wherein the targeting probe is selected from the group consisting of a nucleic acid probe, an antibody, an antibody fragment, and an aptamer; and
   an intracellular delivery ligand attached to the biocompatible coating.

2. The composition of claim 1, wherein the targeting probe is a nucleic acid probe.

3. The composition of claim 2, wherein the nucleic acid probe hybridizes to a nucleic acid target sequence on a subject nucleic acid and forms a stem-loop structure when not bound to the nucleic acid target sequence.

4. The composition of claim 2, wherein the nucleic acid probe comprises a modification of the nucleic acid backbone for the increased stability of the nucleic acid as compared to a naturally occurring nucleic acid.

5. The composition of claim 1, wherein the targeting probe is an antibody or fragment thereof.

6. The composition of claim 1, wherein the targeting probe is an aptamer.

7. The composition of claim 1, wherein the delivery ligand comprises a protein transduction peptide selected from the group consisting of HIV-1 TAT, HSV VP22, and ANTP.

8. The composition of claim 1, wherein the intracellular delivery ligand is selected from the group consisting of the W/R peptide (SEQ ID NO:4), NLS* peptide (SEQ ID NO:5), the AlkCWK18 peptide (SEQ ID NO:6), DiCWK18 peptide (SEQ ID NO:7), the transportan peptide (SEQ ID NO:8), the DipaLytic peptide (SEQ ID NO:9), the K16RGD peptide (SEQ ID NO:10), the P1 peptide (SEQ ID NO:11), the P2 peptide (SEQ ID NO:12), the P3 peptide (SEQ ID NO:13), the P3a peptide (SEQ ID NO:14), the P9.3 peptide (SEQ ID NO:15), the Plae peptide (SEQ ID NO:16), the Kplae peptide (SEQ ID NO:17), the cKplae peptide (SEQ ID NO:18), the MGP peptide (SEQ ID NO:19), the HA2 peptide (SEQ ID NO:20), the LARL46 peptide (SEQ ID NO:21), the Hel-11-7 peptide (SEQ ID NO:22), the KK peptide (SEQ ID NO:23), the KWK peptide (SEQ ID NO:24), the RWR peptide (SEQ ID NO:25), and the Loligomer peptide (SEQ ID NO:26).

9. The composition of claim 1, wherein the intracellular delivery ligand facilitates receptor-mediated endocytosis of the composition.

10. The composition of claim 1, wherein the intracellular delivery ligand facilitates entry into a cell by permeabilizing the cell membrane.

11. The composition of claim 1, wherein the magnetic nanoparticle comprises a metal detectable by use of an MRI instrument that is selected from the group consisting of selected from the group consisting of iron, cobalt, zinc, cadmium, nickel, gadolinium, chromium, copper, manganese, terbium, europium, gold, silver, platinum, and alloys thereof.

12. The composition of claim 11, wherein the magnetic nanoparticle is selected from the group consisting of monocrystalline iron oxide nanoparticle (MION), chelate of gadolinium, and superparamagnetic iron oxide (SPIO).

13. The composition of claim 11, wherein the magnetic nanoparticle is monocrystalline iron oxide nanoparticle (MION).

14. The composition of claim 11, wherein the magnetic nanoparticle is a free metal ion, a metal oxide, a chelate, or an insoluble metal compound.

15. The composition of claim 11, wherein the magnetic nanoparticle is selected from the group consisting of $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary between 1 and 6, depending on the method of synthesis.

16. The composition of claim 11, wherein the magnetic nanoparticle further comprises a metal coating selected from the group consisting of gold, silver, iron, cobalt, zinc, cadmium, nickel, gadolinium, chromium, copper, and manganese, and an alloy thereof.

17. The composition of claim 1, wherein the biocompatible coating is selected from the group consisting of a surfactant based coating, a starch based coating, a dextran based coating, a silica based coating, a layer by layer coating, a phospholipid-polyethylene glycol coating, a polymer coating, a mesoporous particle coating, a microporous particle coating, a lipid based coating, and a dendrimer based coating.

18. The composition of claim 1, wherein the biocompatible coating is a phospholipid-polyethylene glycol coating.

19. The composition of claim 1, wherein the composition further comprises a second delivery ligand that is attached to the biocompatible coating and that interacts with a molecule located on the outer surface of a particular type of cell or tissue.

20. The composition of claim 1, further comprising a second detectable moiety attached to the biocompatible coating, wherein the second detectable moiety is selected from the group consisting of a resonance energy transfer donor moiety; a resonance energy transfer acceptor moiety; a radioisotope; a fluorescent dye; an organic bead, a chelator, or a magnetic nanoparticle with fluorescent or luminescent characteristics; and an inorganic bead with fluorescent or luminescent characteristics.

21. A composition for facilitating signal transduction in molecular imaging or monitoring, comprising:
   a first magnetic nanoparticle probe composition comprising a detectable moiety comprising a magnetic nanoparticle having a biocompatible coating thereon; a first targeting probe attached to the biocompatible coating; and a delivery ligand attached to the biocompatible coating; and
   a second magnetic nanoparticle probe composition comprising a detectable moiety comprising a magnetic nanoparticle having a biocompatible coating thereon; a second targeting probe attached to the biocompatible coating; and a delivery ligand attached to the biocompatible coating;
wherein the first targeting probe binds to a first target and the second targeting probe binds with a second target; and wherein an effect on water relaxation from interaction between the first and second magnetic nanoparticles is detected to determine binding of both the first and the second targeting probes to the first and the second target, and wherein the first magnetic nanoparticle probe composition is different than the second magnetic nanoparticle probe composition.

22. The composition of claim 21, wherein the first targeting probe and the second targeting probe are nucleic acid probes; wherein the first nucleic acid probe hybridizes to a first nucleic acid target sequence on a subject nucleic acid and the second nucleic acid probe hybridizes with a second nucleic acid target sequence on the subject nucleic acid; and wherein the first nucleic acid target sequence and the second nucleic acid target sequence are separated by a number of nucleotides on the subject nucleic acid such that an effect on water relaxation from interaction between the first and second magnetic nanoparticles can be detected to determine hybridization of both the first and the second nucleic acid probes.

23. The composition of claim 22, further comprising
   a third magnetic nanoparticle probe composition comprising a detectable moiety comprising a magnetic nanoparticle having a biocompatible coating thereon; a third targeting probe attached to the biocompatible coating; and a delivery ligand attached to the biocompatible coating; and
   a fourth magnetic nanoparticle probe composition comprising a detectable moiety comprising a magnetic nanoparticle having a biocompatible coating thereon; a fourth targeting probe attached to the biocompatible coating; and a delivery ligand attached to the biocompatible coating;
wherein the third nucleic acid probe hybridizes to a third nucleic acid target sequence on the subject nucleic acid and the fourth nucleic acid probe hybridizes with a fourth nucleic acid target sequence on the subject nucleic acid; and wherein the third nucleic acid target sequence and the fourth nucleic acid target sequence are separated by a number of nucleotides on the subject nucleic acid such that an effect on water relaxation from interaction between the third and fourth magnetic nanoparticles can be detected to determine hybridization of both the third and the fourth nucleic acid probes.

24. The composition of claim 22, wherein the composition further comprises additional magnetic nanoparticle probe pairs.

25. The composition of claim 22, wherein the first nucleic acid probe, the second nucleic acid probe, or both nucleic acid probes hybridize to a nucleic acid target sequence on a subject nucleic acid and form a stem-loop structure when not bound to the nucleic acid target sequence.

26. The composition of claim 22, wherein the first nucleic acid probe, the second nucleic acid probe, or both nucleic acid probes comprise a modification of the nucleic acid backbone for the increased stability of the nucleic acid as compared to a naturally occurring nucleic acid.

27. The composition of claim 21, wherein the first and the second targeting probes are polypeptide probes; wherein the first polypeptide probe binds to a first target sequence on a subject polypeptide and the second polypeptide probe binds with a second target sequence on a subject polypeptide; and wherein the first target sequence and the second target sequence are separated by a distance such that an effect on water relaxation from interaction between the first and second magnetic nanoparticles is detected to determine binding of both the first and the second polypeptide probes.

28. The composition of claim 27, wherein the first and the second target sequences are located on a single subject polypeptide.

29. The composition of claim 27, wherein the first target sequence is located on a first subject polypeptide and the second target sequence is located on a second subject polypeptide; and wherein effect on water relaxation from interaction between the first and second magnetic nanoparticles is detected to determine the interaction of the first subject polypeptide and the second subject polypeptide.

30. The composition of claim 27, wherein the first targeting probe, the second targeting probe, or both targeting probes are antibodies or fragments thereof.

31. The composition of claim 21, wherein the first or the second magnetic nanoparticle probe composition or both comprise two or more targeting probes.

32. The composition of claim 21, wherein the intracellular delivery ligand comprises a cell penetrating peptide selected from the group consisting of HIV-1 TAT, HSV VP22, and ANTP.

33. The composition of claim 21, wherein the intracellular delivery ligand is selected from the group consisting of the W/R peptide (SEQ ID NO:4), the NLS* peptide (SEQ ID NO:5), the AlkCWK18 peptide (SEQ ID NO:6), DiCWK18 peptide (SEQ ID NO:7), the transportan peptide (SEQ ID NO:8), the DipaLytic peptide (SEQ ID NO:9), the K16RGD peptide (SEQ ID NO:10), the P1 peptide (SEQ ID NO:11), the P2 peptide (SEQ ID NO:12), the P3 peptide (SEQ ID NO:13), the P3a peptide (SEQ ID NO:14), the P9.3 peptide (SEQ ID NO:15), the Plae peptide (SEQ ID NO:16), the Kplae peptide (SEQ ID NO:17), the cKplae peptide (SEQ ID NO:18), the MGP peptide (SEQ ID NO:19), the HA2 peptide (SEQ ID NO:20), the LARL46 peptide (SEQ ID NO:21), the Hel-11-7 peptide (SEQ ID NO:22), the KK peptide (SEQ ID NO:23), the KWK peptide (SEQ ID NO:24), the RWR peptide (SEQ ID NO:25), and the Loligomer peptide (SEQ ID NO:26).

34. The composition of claim 21, wherein the magnetic nanoparticle comprises a metal detectable by use of an MRI instrument that is selected from the group consisting of selected from the group consisting of iron, cobalt, zinc, cadmium, nickel, gadolinium, chromium, copper, manganese, terbium, europium, gold, silver, platinum, and alloys thereof.

35. The composition of claim 34, wherein the magnetic nanoparticle is monocrystalline iron oxide nanoparticle (MION).

36. The composition of claim 34, wherein the magnetic nanoparticle is a free metal ion, a metal oxide, a chelate, or an insoluble metal compound.

37. The composition of claim 34, wherein the magnetic nanoparticle is selected from the group consisting of $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary between 1 and 6 depending on the method of synthesis.

38. The composition of claim 34, wherein the magnetic nanoparticle further comprises a metal coating selected from the group consisting of gold, silver, iron, cobalt, zinc, cadmium, nickel, gadolinium, chromium, copper, manganese, and an alloy thereof.

39. The composition of claim 21, wherein the biocompatible coating is selected from the group consisting of a surfactant based coating, a starch based coating, a dextran based coating, a silica based coating, a layer by layer coating, a phospholipid-polyethylene glycol coating, a polymer coating, a mesoporous particle coating, a microporous particle coating, a lipid based coating, and a dendrimer based coating.

40. The composition of claim 21, wherein the biocompatible coating is a phospholipid-polyethylene glycol coating.

41. The composition of claim 21, wherein the first magnetic nanoparticle probe composition, the second magnetic nanoparticle probe composition, or both further comprise a second delivery ligand that is attached to the biocompatible coating and that interacts with a molecule located on the outer surface of a particular type of cell or tissue.

42. The composition of claim 21, wherein the first magnetic nanoparticle probe composition, the second magnetic nanoparticle probe composition, or both further comprise a second detectable moiety attached to the biocompatible coating, wherein the detectable moiety is selected from the group consisting of a resonance energy transfer donor or acceptor moiety, a fluorescent dye, an organic bead with fluorescent or luminescent characteristics, and an inorganic bead with fluorescent or luminescent characteristics.

43. The composition of claim 21, wherein the first magnetic nanoparticle probe composition, the second magnetic nanoparticle probe composition, or both further comprise a therapeutic molecule attached to the biocompatible coating or to the magnetic nanoparticle.

44. A composition for facilitating molecular imaging, comprising two or more magnetic nanoparticle probe compositions within a vesicle, wherein each magnetic nanoparticle probe composition comprises at least one targeting probe and a detectable moiety attached thereto, wherein the detectable moiety comprises a magnetic nanoparticle having a biocompatible coating thereon, and wherein the vesicle comprises a biocompatible membrane having at least one delivery ligand on its outer surface.

45. A method for producing a magnetic nanoparticle probe composition for facilitating molecular imaging, comprising:
combining a magnetic nanoparticle with a biocompatible coating;
adding an intracellular delivery ligand; and
adding a targeting probe, wherein the targeting probe is selected from the group consisting of a nucleic acid probe, an antibody, an antibody fragment, and an aptamer.

46. The method of claim 45, wherein the intracellular delivery ligand is selected from the group consisting of the HIV-1 TAT peptide (SEQ ID NO:1), the HSV VP22 peptide (SEQ ID NO:2), the ANTP peptide (SEQ ID NO:3), the W/R peptide (SEQ ID NO:4), the NLS* peptide (SEQ ID NO:5), the AlkCWK18 peptide (SEQ ID NO:6), DiCWK18 peptide (SEQ ID NO:7), the transportan peptide (SEQ ID NO:8), the DipaLytic peptide (SEQ ID NO:9), the K16RGD peptide (SEQ ID NO:10), the P1 peptide (SEQ ID NO:11), the P2 peptide (SEQ ID NO:12), the P3 peptide (SEQ ID NO:13), the P3a peptide (SEQ ID NO:14), the P9.3 peptide (SEQ ID NO:15), the Plae peptide (SEQ ID NO:16), the Kplae peptide (SEQ ID NO:17), the cKplae peptide (SEQ ID NO:18), the MGP peptide (SEQ ID NO:19), the HA2 peptide (SEQ ID NO:20), the LARL46 peptide (SEQ ID NO:21), the Hel-11-7 peptide (SEQ ID NO:22), the KK peptide (SEQ ID NO:23), the KWK peptide (SEQ ID NO:24), the RWR peptide (SEQ ID NO:25), and the Loligomer peptide (SEQ ID NO:26).

47. The method of claim 45, wherein the magnetic nanoparticle comprises a metal detectable by an MRI instrument that is selected from the group consisting of selected from the group consisting of iron, cobalt, zinc, cadmium, nickel, gadolinium, chromium, copper, and manganese.

48. The method of claim 45, wherein the magnetic nanoparticle is monocrystalline iron oxide nanoparticle (MION).

49. The method of claim 45, wherein the biocompatible coating is selected from the group consisting of a surfactant based coating, a starch based coating, a dextran based coating, a silica based coating, a layer by layer coating, a phospholipid-polyethylene glycol coating, a polymer coating, a mesoporous particle coating, a microporous particle coating, a lipid based coating, and a dendrimer based coating.

50. The method of claim 45, wherein the biocompatible coating is a phospholipid-polyethylene glycol coating.

51. The method of claim 45, further comprising the step of adding a second delivery ligand to the biocompatible coating that interacts with a molecule located on the outer surface of a particular type of cell or tissue.

52. The method of claim 45, further comprising the step of adding a therapeutic molecule to the biocompatible coating.

53. A nanoparticle probe composition for facilitating molecular imaging or monitoring, comprising:
a detectable moiety comprising a magnetic nanoparticle having a biocompatible coating thereon;
a targeting probe attached to the biocompatible coating; and
an intracellular delivery ligand attached to the biocompatible coating,
wherein the intracellular delivery ligand is selected from the group consisting of the HSV VP22 peptide (SEQ ID NO:2), the ANTP peptide (SEQ ID NO:3), the W/R peptide (SEQ ID NO:4), the NLS* peptide (SEQ ID NO:5), the AlkCWK1S peptide (SEQ ID NO:6), the DiCWK18 peptide (SEQ ID NO:7), the transportan peptide (SEQ ID NO:8), the DipaLytic peptide (SEQ ID NO:9), the KI6RGD peptide (SEQ ID NO:1O), the P1 peptide (SEQ ID 10:11), the P2 peptide (SEQ ID NO:12), the P3 peptide (SEQ ID NO:13), the P3a peptide (SEQ ID NO:14), the P9.3 peptide (SEQ ID NO:15), the Plac peptide (SEQ ID NO:16), the Kplae peptide (SEQ ID NQ:17), the cKplae peptide (SEQ ID NO: 18), the MGP peptide (SEQ ID NO: 19), the HA2 peptide (SEQ ID NO:20), the LARL46 peptide (SEQ ID NO:21), the Hel-l1-7 peptide (SEQ ID NO:22), the KK peptide (SEQ ID NO:23), the KWK peptide (SEQ ID NO:24), the RWR peptide (SEQ ID NO:2 5), and the Loligomer peptide (SEQ ID NO:26).

54. A method for producing a magnetic nanoparticle probe composition for facilitating molecular imaging, comprising:

combining a magnetic nanoparticle with a biocompatible coating;

adding a targeting probe; and adding an intracellular delivery ligand;

wherein the intracellular delivery ligand is selected from the group consisting of the HSV VP22 peptide (SEQ ID NO:2), the ANTP peptide (SEQ ID NO:3), the W/R peptide (SEQ ID NO:4), the NLS* peptide (SEQ ID NO:5), the AlkCWKI8 peptide (SEQ ID NO:6), the DiCWK18 peptide (SEQ ID NO:7), the transportan peptide (SEQ ID NO:8), the DipaLytic peptide (SEQ ID NO:9), the K16RGD peptide (SEQ ID NO:10), the P1 peptide (SEQ ID NO:11 ), the P2 peptide (SEQ ID NO:12), the P3 peptide (SEQ ID NO:13), the P3a peptide (SEQ ID NO:14), the P9.3 peptide (SEQ ID NO:15), the Plae peptide (SEQ ID NO:16), the Kplae peptide (SEQ ID NO:17). the cKplae peptide (SEQ ID NO:18), the MGP peptide (SEQ ID NO:19), the HA2 peptide (SEQ ID NO:20), the LARL46 peptide (SEQ ID NO:21), the Hel-11-7 peptide (SEQ ID NO:22), the KK peptide (SEQ ID NO:23), the KWK peptide (SEQ ID NO:24), the Rfl peptide (SEQ ID NO:25), and the Loligomer peptide (SEQ ID N0:26).

* * * * *

UNITED STATES PATENT AND TRADEMARK OFFICE
CERTIFICATE OF CORRECTION

PATENT NO. : 7,459,145 B2 Page 1 of 1
APPLICATION NO. : 10/694243
DATED : December 2, 2008
INVENTOR(S) : Gang Bao et al.

It is certified that error appears in the above-identified patent and that said Letters Patent is hereby corrected as shown below:

At column 51, line 36, delete "a" and insert --an intracellular--.

At column 51, line 42, delete "a" and insert --an intracellular--.

At column 52, line 2, delete "a" and insert --an intracellular--.

At column 52, line 8, delete "a" and insert --an intracellular--.

At column 55, line 3, delete "10" after "P1 peptide(SEQ ID 10:11)" and insert --NO:--

At column 55, line 11, delete "2 5" and insert --25--.

At column 56, line 16, delete "Rfl" and insert --RWR--.

Signed and Sealed this

Eighth Day of June, 2010

David J. Kappos
*Director of the United States Patent and Trademark Office*

SEQUENCE LISTING

<160> NUMBER OF SEQ ID NOS: 32

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Tyr Gly Arg Lys Lys Arg Arg Gln Arg Arg
 1               5                  10

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ala Ala Thr Ala Thr Arg Gly Arg Ser Ala Ala Ser Arg Pro Thr
 1               5                  10                  15

Glu Arg Pro Arg Ala Pro Ala Arg Ser Ala Ser Arg Pro Arg Arg Pro
            20                  25                  30

Val Glu

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gln Ile Lys Ile Trp Phe Gln Asn Arg Arg Met Lys Trp Lys Lys
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Trp Arg Arg Trp Trp Arg Arg Trp Trp Arg Arg Trp Arg Arg
 1               5                  10                  15

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Pro Pro Lys Lys Lys Arg Lys Val Glu Asp Pro
 1               5                  10

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Trp Lys Lys Lys Lys Lys Lys Lys Lys Lys Lys Lys Lys Lys Lys
 1               5                  10                  15
```

-continued

```
Lys Lys Lys Lys
            20

<210> SEQ ID NO 7
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Lys Lys Lys Lys Lys Lys Lys Lys Lys Lys Lys Lys Lys Lys
 1               5                  10                  15

Lys Lys Trp Cys Cys Trp Lys Lys Lys Lys Lys Lys Lys Lys
            20                  25                  30

Lys Lys Lys Lys Lys Lys Lys Lys
         35                  40

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Leu Phe Glu Ala Leu Glu Glu Leu Trp Glu Ala Lys
 1               5                  10

<210> SEQ ID NO 10
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Lys Lys Lys Lys Lys Lys Lys Lys Lys Lys Lys Lys Lys
 1               5                  10                  15

Gly Gly Cys Arg Gly Asp Met Phe Gly Cys Ala Lys Lys Lys Lys
            20                  25                  30

Lys Lys Lys Lys Lys Lys Lys Lys Lys Lys Arg Gly Asp
         35                  40                  45

<210> SEQ ID NO 11
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Lys Lys Lys Lys Lys Lys Lys Lys Lys Lys Lys Lys Lys Lys Lys
  1               5                  10                  15

Gly Gly Cys Met Phe Gly Cys Gly Gly
             20                  25

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Lys Lys Lys Lys Lys Lys Lys Lys Lys Lys Lys Lys Lys
  1               5                  10                  15

Ile Cys Arg Arg Ala Arg Gly Asp Asn Pro Asp Asp Arg Cys Thr
             20                  25                  30

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)
<223> OTHER INFORMATION: Beta-Ala
<220> FEATURE:
<221> NAME/KEY: MOD_RES
<222> LOCATION: (19)
<223> OTHER INFORMATION: Lys coupled to biotin (D-biocytin)
<220> FEATURE:
<221> NAME/KEY: MOD_RES
<222> LOCATION: (20)
<223> OTHER INFORMATION: Beta-Ala

<400> SEQUENCE: 13

Lys Lys Trp Lys Met Arg Arg Asn Gln Phe Trp Val Lys Val Gln Arg
  1               5                  10                  15

Ala Lys Xaa Ala
             20

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ala Tyr Ile Ser Arg Gly Gly Val Ser Thr Tyr Ser Asp Thr
  1               5                  10                  15

Val Lys Gly Arg Phe Thr Arg Gln Lys Tyr Asn Lys Arg Ala
             20                  25                  30

<210> SEQ ID NO 15
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Gly Arg Ile Asp Pro Ala Asn Gly Lys Thr Lys Tyr Ala Pro Lys
 1               5                  10                  15

Phe Gln Asp Lys Ala Thr Arg Ser Asn Tyr Tyr Gly Asn Ser Pro Ser
                20                  25                  30

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Leu Ala Glu Ile Asp Gly Ile Glu Leu Thr Tyr
 1               5                  10

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Lys Lys Lys Lys Lys Lys Lys Lys Lys Lys Lys Lys Lys Lys Lys
 1               5                  10                  15

Gly Gly Pro Leu Ala Glu Ile Asp Gly Ile Glu Leu Gly Ala
                20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Lys Lys Lys Lys Lys Lys Lys Lys Lys Lys Lys Lys Lys Lys
 1               5                  10                  15

Gly Gly Pro Leu Ala Glu Ile Asp Gly Ile Glu Leu Cys Ala
                20                  25                  30

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ala Leu Phe Leu Gly Phe Leu Gly Ala Ala Gly Ser Thr Met
 1               5                  10                  15

Gly Ala Trp Ser Gln Pro Lys Ser Lys Arg Lys Val
                20                  25
```

```
<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Glu Ala Lys Leu Ala Lys Ala Leu Ala Lys Ala Leu Ala Lys His
 1               5                  10                  15

Leu Ala Lys Ala Leu Ala Lys Ala Leu Lys Ala Cys
            20                  25

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Ala Arg Leu Leu Ala Arg Leu Leu Ala Arg Leu Leu Ala Arg Leu
 1               5                  10                  15

Leu Ala Arg Leu Leu Ala Arg Leu
            20

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Leu Leu Lys Leu Leu Leu Lys Leu Trp Leu Lys Leu Leu Lys Leu
 1               5                  10                  15

Leu Leu

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Lys Lys Lys Lys Lys Lys Lys Gly Gly Cys
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Trp Lys Lys Lys Trp Lys Lys Gly Cys Cys
 1               5                  10
```

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Trp Arg Arg Arg Trp Arg Arg Gly Gly Cys
 1               5                  10

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Lys Lys Lys Lys Lys Lys Lys Lys Lys Lys Lys Lys Lys Lys
 1               5                  10                  15

Lys Lys Lys Lys Lys Lys Lys Gly Gly Lys Lys Lys Lys Pro Asp
            20                  25                  30

Glu Val Lys Arg Lys Lys Lys Pro Pro Thr
            35                  40

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetc
      probe

<400> SEQUENCE: 27
gagtccttcc acgatactac gatccacatt                                      30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetc
      probe

<400> SEQUENCE: 28
aatgtggatc gtagtatcgt cgaaggactc                                      30

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gly Arg Lys Lys Arg Arg Gln Arg Arg Arg
 1               5                  10

<210> SEQ ID NO 30
<211> LENGTH: 26
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 30
cgacggagtc cttccacgat accacg                                          26

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgacggagaa agggctgcca cg                                              22

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgacgcgaca agcgcaccga tacg                                            24
```